US011439684B2

(12) United States Patent
Porrata et al.

(10) Patent No.: US 11,439,684 B2
(45) Date of Patent: Sep. 13, 2022

(54) LYMPHOCYTE AND MONOCYTE POPULATIONS IN CANCER PATIENTS AND AUTOLOGOUS STEM CELL PREPARATIONS, AND USES THEREOF

(71) Applicant: Mayo Foundation for Medical Education and Research, Rochester, MN (US)

(72) Inventors: Luis F. Porrata, Rochester, MN (US); Svetomir N. Markovic, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/486,863

(22) PCT Filed: Feb. 20, 2018

(86) PCT No.: PCT/US2018/018744
§ 371 (c)(1),
(2) Date: Aug. 19, 2019

(87) PCT Pub. No.: WO2018/156493
PCT Pub. Date: Aug. 30, 2018

(65) Prior Publication Data
US 2020/0230209 A1    Jul. 23, 2020

Related U.S. Application Data

(60) Provisional application No. 62/461,663, filed on Feb. 21, 2017.

(51) Int. Cl.
*A61K 38/20* (2006.01)
*A61K 45/06* (2006.01)
(52) U.S. Cl.
CPC .......... *A61K 38/2086* (2013.01); *A61K 38/20* (2013.01); *A61K 45/06* (2013.01)
(58) Field of Classification Search
CPC .......... G01N 2333/70535; G01N 2333/70539; G01N 33/5005; G01N 33/56972; G01N 2333/70596; G01N 33/5044
See application file for complete search history.

(56) References Cited

U.S. PATENT DOCUMENTS

| | | | |
|---|---|---|---|
| 4,499,052 A | 2/1985 | Fulwyler | |
| 5,125,737 A | 6/1992 | Rodriguez et al. | |
| 5,595,756 A * | 1/1997 | Bally | A61K 9/1272 264/4.1 |
| 2010/0316599 A1 | 12/2010 | Nelson et al. | |
| 2012/0171207 A1 | 7/2012 | Wilcox et al. | |

FOREIGN PATENT DOCUMENTS

| | | |
|---|---|---|
| WO | WO 2006/004592 | 1/2006 |
| WO | WO 2013/169693 | 11/2013 |
| WO | WO 2017/053671 | 3/2017 |
| WO | WO 2017/062107 | 4/2017 |

OTHER PUBLICATIONS

Porrata et al. Infused autograft lymphocyte to monocyte ratio predicts survival in classical Hodgkin lymphoma. J Blood Med. 2015;6: 45-53. (Year: 2015).*
Porrata et al. Early Lymphocyte Recovery Predicts Superior Survival after Autologous Stem Cell Transplantation in Non-Hodgkin Lymphoma: A Prospective Study. Biology of Blood and Marrow Transplantation 14:807-816 (2008) (Year: 2008).*
Rueff et al. Lymphoma subset recovery and outcome after autologous hematopoietic stem cell transplanation for plasma cell myeloma. Biol Blood Marrow Transplant 20 (2014) 881e90 (Year: 2014).*
Porrata. Autologous Graft-versus-Tumor Effect: Reality or Fiction? Advances in Hematology vol. 2016, Article ID 5385972, 8 pages (Year: 2016).*
Lin et al. Immunosuppressive CD14+HLA-DRlow-/- monocytes in B-cell non-Hodgkin lymphoma. Blood, 2011; 117(3):872-881 (Year: 2011).*
Mougiakakos et al. Leukemia, 2013, 27:377-388 (Year: 2013).*
Omazic et al. Long-Term Follow-Up of Allogeneic Hematopoietic Stem Cell Transplantation for Solid Cancer. Biol Blood Marrow Transplant 22(2016); 676-681 (Year: 2016).*
Heppner et al. Tumor heterogeneity: biological implications and therapeutic consequences. Cancer Metastasis Review 2:5-23; 1983 (Year: 1983).*
Jain RK. Barriers to drug delivery in solid tumors. Scientific American, Jul. 1994, 58-65 (Year: 1994).*
Perini et al. Lymphocyte: monocyte ratio at the start of conditioning regimen is associated with surviviai post-autologous stem cell transplantation for lymphoma and myeloma. Blood, 2013; 122(21):3327 (Year: 2013).*
Perini et al. Lymphocyte:monocyte ratio at the start of conditioning regimen is associated with survival post-autologous stem cell transplantation for lymphoma and myeloma. Blood, 2013; 122(21):3327 (Year: 2013) (Year: 2013).*
Lin et al. Immunosuppressive CD14+HLA-DRlow/−monocytes in B-cell non-Hodgkin lymphoma. Blood. Jan. 2, 2011; 117(3): 872-881 (Year: 2011).*
Bungart et al., "Differential effects of recombinant human colony stimulating factor (rh G-CSF) on stem cells in marrow, spleen and peripheral blood in mice," Br. J. Haematol., 76(2):174-9, Oct. 1990.
Cheson et al., "Revised response criteria for malignant lymphoma," J. Clin. Oncol., 25(6):579-86, Feb. 2007.
Cox, "Regression models and life-tables," Journal of the Royal Statistical Society: Series B (Methodological), 34(2):187-202, Jan. 1972.
Grzegorzewski et al., "Administration of recombinant human interleukin-7 to mice induces the exportation of myeloid progenitor cells from the bone marrow to peripheral sites," Blood, 83:377-85, 1994.

(Continued)

*Primary Examiner* — Vanessa L. Ford
*Assistant Examiner* — Sandra Dillahunt
(74) *Attorney, Agent, or Firm* — Fish & Richardson P.C.

(57) ABSTRACT

Provided herein are materials and methods for assessing ratios of lymphocyte to monocytes in cancer patients and, based on the ratios, treating the cancer patients with an immunotherapeutic.

5 Claims, 10 Drawing Sheets

(56) References Cited

OTHER PUBLICATIONS

Hillyer et al., "CD34+ progenitors and colony-forming units-granulocyte macrophage are recruited during large-volume leukapheresis and concentrated by counterflow centrifugal elutriation," Transfusion, 33(4):316-321, Apr. 1993.
Hoechst et al., "Myeloid derived suppressor cells inhibit natural killer cells in patients with hepatocellular carcinoma via the NKp30 receptor," Hepatology, 50(3):799-807, Aug. 2009.
Jackson et al., "Interleukin-12 enhances peripheral hematopoiesis in vivo," Blood, 85(9):2371-6, 1995.
Kansagra et al., "65 Infusion of autograft natural killer cells/CDM+ hla-DR/\DIM myeloid-derived suppressor cells ratio predicts survival in non-Hodgkin lymphoma undergoing autologous peripheral blood hematopoietic stem cell transplantation (APHSCT)," Biol, Blood Marrow Transplant., 23(3):SS66-7, Feb. 2017.
Kansagra et al. "Infusion of autograft natural killer cell/CD14+ HLA-DR'/\DIM cell ratio predicts survival in lymphoma post autologous stem cell transplantation," Bone Marrow Transplant., 53:146-54, Oct. 2017.
Kaplan and Meier, "Nonparametric estimation from incomplete observations," J. Am, Stat. Assoc., 53(282):457-81, Jun. 1958.
Kaufman et al., "The absolute lymphocyte/monocyte ratio recovery during ABVD treatment cycles is not significantly impacted by the use of myeloid growth factors and predicts clinical outcomes in classical Hodgkin lymphoma regardless of their use," Blood Lymphatic Cancer: Targ. Ther., 4:39, 2014.
Kersey et al., "Comparison of autologous and allogeneic bone marrow transplantation for treatment of high-risk refractory acute lymphoblastic leukemia," N. Engl. J. Med., 317(8):416-67, Aug. 1987.
Lane et al., "Harvesting and enrichment of hematopoietic progenitor cells mobilized into the peripheral blood of normal donors by granulocyte-macrophage colony-stimulating factor (GM-CSF) or G-CSF: Potential role in allogeneic marrow transplantation," Blood, 85(1):275-282, Jan. 1991.
Laterveer et al., "Interleukin-8 induces rapid mobilization of hematopoietic stem cells with radioprotective capacity and long-term myelolymphoid repopulating ability," Blood 85(8):2269-75, Apr. 1995.
Lin et al. "Immunosuppressive CD14+HLA-DR(low/-) monocytes in B-cell non-Hodgkin lymphoma," Blood, 117(3):872-81, Jan. 2011.
Lyman et al., "Cloning of the human homologue of the murine flt3 ligand: a growth factor for early hematopoietic progenitor cells," Blood 83(10):2795-801, May 1994.
Marmont et al., "T-cell depletion of HLA-identical transplants in leukemia," Blood, 78(8):2120-30, Oct. 1991.
PCT International Preliminary Report on Patentability in International Appln. No. PCT/US2018/018744 dated Sep. 6, 2019, 13 pages.
PCT International Search Report and Written Opinion in International Appln. No. PCT/US2018/018744 dated May 18, 2018, 16 pages.
Perini et al., "Lymphocyte: Monocyte ratio at the start of conditioning regimen is associated with survival post-autologous stem cell transplantation (ASCT) for lymphoma and myeloma," Blood, 122(21):3327, Dec. 2013.
Porrata et al., "Interleukin-15 affects patient survival through natural killer cell recovery after autologous hematopoietic stem cell transplantation for non-Hodgkin lymphomas," Clin. Develop. Immunol., 2010:914945, Apr. 2010.
Porrata et al., "Autologous graft-versus-tumor effect: Reality or fiction?," Adv. Hematol., 2016:5385972, Jul. 2016.
Porrata et al., "Day 15 peripheral blood lymphocyte/monocyte ratio post-autologous peripheral hematopoietic stem cell transplantation and survival in diffuse large B-cell lymphoma," J. Stem Cell Res. Ther., 1(2):1000103, 2011.
Porrata et al., "Immunologic autograft engineering and survival in non-Hodgkin lymphoma," Biol. Blood Marrow Transplant., 22(6):1017-23, Jun. 2016.
Porrata et al., "Infused autograft lymphocyte to monocyte ratio and survival in diffuse large B cell lymphoma," Biol. Blood Marrow Transplant., 20:1804-12, 2014.
Porrata et al., "Peripheral blood absolute lymphocyte/monocyte ratio during rituximab, cyclophosphamide, doxorubicin, vincristine and prednisone treatment cycles predicts clinical outcomes in diff use large B-cell lymphoma," Leukemia Lymphoma, 55(12):2728-38, Dec. 2014.
Porrata et al., "Peripheral blood lymphocyte/monocyte ratio at diagnosis and survival in classical Hodgkin's lymphoma," Haematologica, 97(2):1-8, 2012.
Sudo et al., "Synergistic Effect of FLT-3 Ligand on the Granulocyte Colony-Stimulating Factor-Induced Mobilization of Hematopoietic Stem Cells and Progenitor Cells Into Blood in Mice," Blood 89(9):3186-91, May 1997.
Terella et al., "Role of chemotherapy and GM-CSF on hemopoietic progenitor cell mobilization in multiple myeloma," Bone Marrow Transplant, 11(4):271-7, Apr. 1993.
The International Non-Hodgkin's Lymphoma Prognostic Factors Project, "A predictive model for aggressive non-Hodgkin's lymphoma.," N. Engl. J. Med., 329(14):987-94, Sep. 1993.
Tzankov et al., "Prognostic immunophenotypic biomarker studies in diffuse large B cell lymphoma with special emphasis on rational determination of cut-off scores," Leukemia Lymphoma, 51(2):199-212, Feb. 2010.
Wilcox et al., "The absolute monocyte and lymphocyte prognostic score predicts survival and identifies high-risk patients in diffuse large-B-cell lymphoma," Leukemia, 25(9):1502, Sep. 2011.
Williams et al., "Peripheral blood-derived stem cell collections for use in autologous transplantation after high dose chemotherapy: an alternative approach.," Bone Marrow Transplant., 5(2):129-33, Feb. 1990.
Azzaoui et al., "T-cell defect in diffuse large B-cell lymphomas involves expansion of myeloid-derived suppressor cells," Blood, 128(8):1081-1092, Aug. 25, 2016.
Boulassel et al., "Early lymphocyte recovery following autologous peripheral stem cell transplantation is associated with better survival in younger patients with lymphoproliferative disorders," Hematology, 11(3)165-170, Jun. 2006.
Dienz et al., "The effects of IL-6 on CD4 T cell responses," Clin. Immunology, 130(1):27-33, Jan. 2009.
Doocey et al., "Allogeneic haematopoietic stem-cell transplantation for relapsed and refractory aggressive histology non-Hodgkin lymphoma," Br. J. Hematology, 131(2):223-230.
Fehniger et al., "Interleukin 15: biology and relevance to human disease," Blood, 97(1):14-32, Jan. 1, 2001.
Ferrandina et al., "Lymphocyte recovery in advanced ovarian cancer patients after high-dose chemotherapy and peripheral blood stem cell plus growth factor support: clinical implications," Clin. Cancer Research, 9(1):195-200, Jan. 2003.
Gordan et al., "Correlation of early lymphocyte recovery and progression-free survival after autologous stemcell transplant in patients with Hodgkin's and non-Hodgkin's lymphoma," Bone Marrow Transplantation, 31(11):1009-1013, Jun. 2003.
Holtan et al., "AMD3100 affects autograft lymphocyte collection and progression-free survival after autologous stem cell transplantation in non-Hodgkin lymphoma," Clin. Lymphoma Myeloma, 7(4):315-318, Jan. 2007.
Joao et al., "Early lymphocyte recovery after autologous stem cell transplantation predicts superior survival in mantle-cell lymphoma," Bone Marrow Transplantation, 37(9):865-871.
Kim et al., "Early lymphocyte recovery predicts longer survival after autologous peripheral blood stem cell transplantation in multiple myeloma," Bone Marrow Transplantation, 37(11):1037-1042, Jun. 2006.
Kim et al., "Lymphocyte recovery as a positive predictor of prolonged survival after autologous peripheral blood stem cell transplantation in T-cell non-Hodgkin's lymphoma," Bone Marrow Transplantation, 34(1):43-49, Jul. 2004.

(56) References Cited

OTHER PUBLICATIONS

Lin et al., "Immunosuppressive CD14+HLA-DR(low)/− monocytes in B-cell non-Hodgkin lymphoma," Blood, 117(3):872-881, Jan. 20, 2011.

Nieto et al., "Prognostic analysis of early lymphocyte recovery in patients with advanced breast cancer receiving high-dose chemotherapy with an autologous hematopoietic progenitor cell transplant," Clin. Cancer Research, 10(15):5076-5086.

Parish-Novak et al., "Interleukin 21 and its receptor are involved in NK cell expansion and regulation of lymphocyte function," Nature, 408(6806):57-63, Nov. 2, 2000.

Philip et al., "Autologous Bone Marrow Transplantation as Compared with Salvage Chemotherapy in Relapses of Chemotherapy-Sensitive Non-Hodgkin's Lymphoma," N. Eng. J. Medicine, 333(23):1540-1545, Dec. 7, 1995.

Porrata et al., "Early lymphocyte recovery post-autologous haematopoietic stem cell transplantation is associated with better survival in Hodgkin's disease," Br. J. Haematology, 117(3):629-633, Jun. 2002.

Porrata et al., "Timely reconstitution of immune competence affects clinical outcome following autologous stem cell transplantation," Clin. Exp. Medicine, 4(2):78-85, Oct. 2004.

Porrata et al., "Autograft mediated adoptive immunotherapy of cancer in the context of autologous stem cell transplantation," World J. Clin. Oncology, 1(1):29-34, Nov. 10, 2010.

Porrata et al., "Infused peripheral blood autograft absolute lymphocyte count correlates with day 15 absolute lymphocyte count and clinical outcome after autologous peripheral hematopoietic stem cell transplantation in non-Hodgkin's lymphoma," Bone Marrow Transplantation, 33(3):291-298, Feb. 2004.

Porrata et al., "Prolonged survival associated with early lymphocyte recovery after autologous hematopoietic stem cell transplantation for patients with metastatic breast cancer," Bone Marrow Transplantation, 28(9):865-871, Nov. 2001.

Porrata et al., "Sustained Natural Killer Cell Recovery Post-Autologous Peripheral Blood Hematopoietic Stem Cell Transplantation Predicts Survival in Non-Hodgkin's Lymphoma," Presented at Proceedings of the 58th ASH Annual Meeting and Exposition, San Diego, CA, Dec. 3-6, 2016; Blood, 128(22):4641, Dec. 2, 2016.

Porrata et al., "The dose of infused lymphocytes in the autograft directly correlates with clinical outcome after autologous peripheral blood hematopoietic stem cell transplantation in multiple myeloma," Leukemia, 18(6): 1085-1092, Jun. 2004.

Porrata et al., "Early lymphocyte recovery is a predictive factor for prolonged survival after autologous hematopoietic stem cell transplantation for acute myelogenous leukemia," Leukemia, 16(7):1311-1318, Jul. 2002.

Porrata et al., "Early lymphocyte recovery predicts superior survival after autologous hematopoietic stem cell transplantation for patients with primary systemic amyloidosis," Clin. Cancer Research, 11(3):1210-1218, Feb. 2005.

Porrata et al., "Early lymphocyte recovery predicts superior survival after autologous hematopoietic stem cell transplantation in multiple myeloma or non-Hodgkin lymphoma," Blood, 98(3):579-585, Aug. 1, 2001.

Valtola et al., "Early immune recovery after autologous transplantation in nonHodgkin lymphoma patients: predictive factors and clinical significance," Leuk. Lymphoma, 57(9):2025-2032, Sep. 2016.

\* cited by examiner

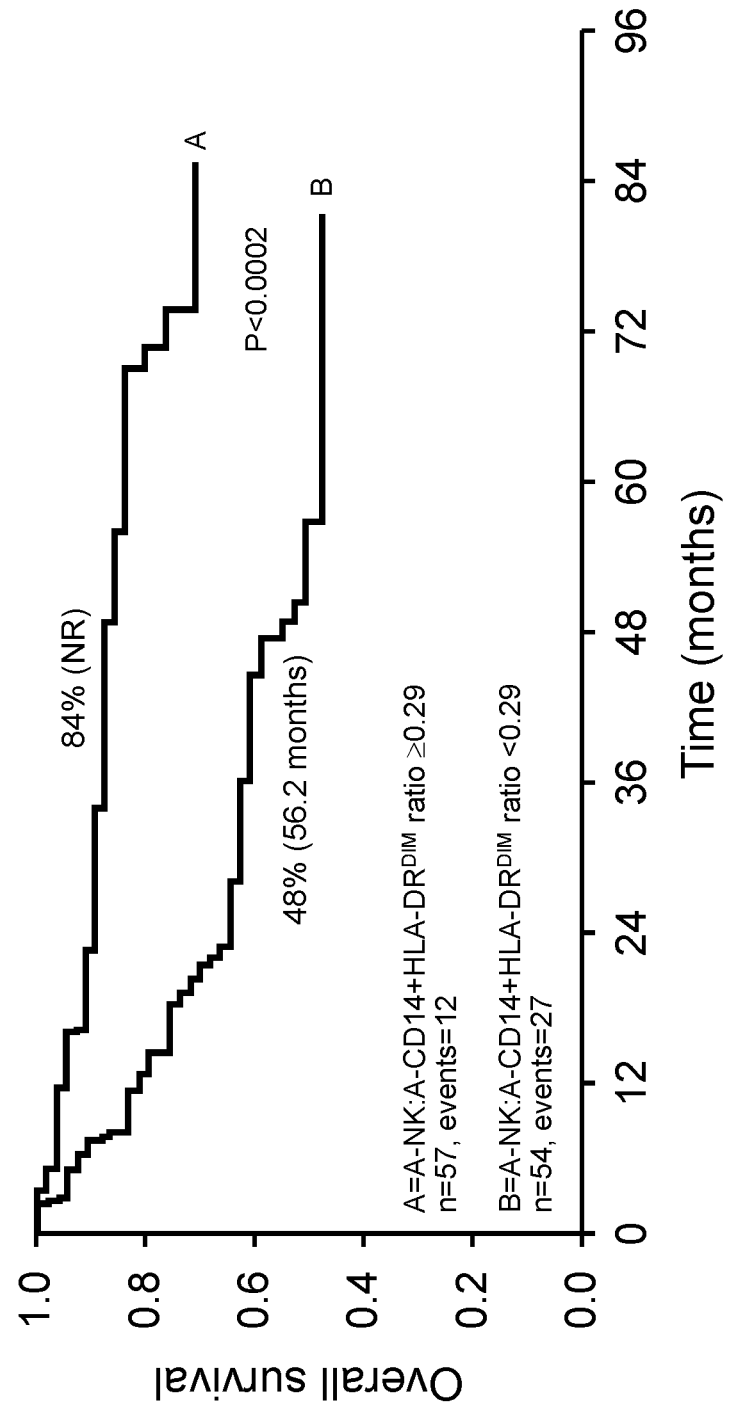

LYMPHOCYTE AND MONOCYTE POPULATIONS IN CANCER PATIENTS AND AUTOLOGOUS STEM CELL PREPARATIONS, AND USES THEREOF

CROSS-REFERENCE TO RELATED APPLICATIONS

This application is a National Stage application under 35 U.S.C. § 371 of International Application No. PCT/US2018/018744, having an International Filing Date of Feb. 20, 2018, which claims benefit of priority from U.S. Provisional Application Ser. No. 62/461,663, filed Feb. 21, 2017. The disclosures of the prior applications are considered part of (and are incorporated by reference in) the disclosure of this application.

TECHNICAL FIELD

This document relates to materials and methods for assessing the lymphocyte to monocyte ratio (LMR) in cancer patients, and for treating cancer patients an immunostimulatory agent when the LMR is at least 1.0.

BACKGROUND

Autologous peripheral blood hematopoeitic stem cell transplantation (APBHSCT) can improve survival in various types of cancer, including myelomas and leukemias [e.g., acute lymphoblastic leukemia (ALL) and acute myeloid leukemia (AML)], as well as Hodgkin and non-Hodgkin's lymphomas [e.g., diffuse large B-cell lymphoma (DLBCL)], whether the APBHSCT is carried out before, after, or without chemotherapy.

High relapse rates post-APBHSCT, however, have been attributed to the inability of high dose therapy (HDT) to eradicate minimal residual disease. In contrast, allogeneic stem cell transplantation following chemotherapy results in lower relapse rates, which have been correlated to early absolute lymphocyte count (ALC) recovery as a manifestation of early graft-versus-tumor effect in the recipient (Kersey et al. (1987) *New Engl J Med* 317:416; Marmont et al. (1991) *Blood* 78:2120). Allogeneic stem cell transplantation has also, however, been associated with a higher incidence of graft-versus-host disease (GVHD), thus leading to higher allogeneic transplant-related mortality in comparison to APBHSCT.

SUMMARY

This document is based, at least in part, on the discovery that the lymphocyte to monocyte ratio in infused autologous stem cell transplants (A-LMR), as well as the lymphocyte to monocyte ratio (LMR) achieved in patients treated by APBHSCT, can be used as an indicator of prognosis, and also as the impetus for treating a transplant recipient with an immunostimulatory agent [e.g., interleukin-15 (IL-15) or interleukin-21 (IL-21), or a combination thereof]. For example, a LMR that is less than 1.0 can be used as an indicator that a patient has a worse prognosis than a patient with a LMR of 1.0 or greater (e.g., such that the patient with a LMR less than 1.0 has a lower chance of progression-free survival or overall survival than a patient with a LMR of at least 1.0). The LMR also can be used as an indicator that a patient should be treated with an immunotherapeutic that can increase the absolute lymphocyte count (ALC) in the patient, reduce the absolute monocyte count (AMC) in the patient, or both.

In addition, this document is based, at least in part, on the discovery that the autograft absolute monocyte count (A-AMC) in infused autologous stem cell transplants (A-AMC), as well as the AMC recovery post-APBHSCT, can be used as an indicator of prognosis. For example, a patient receiving APBHSCT having an A-AMC that is more than $0.5 \times 10^9$ cells/kg may have a worse prognosis than a patient receiving APBHSCT having an A-AMC of $0.5 \times 10^9$ cells/kg or less. In some cases, an A-AMC greater than $0.5 \times 10^9$ cells/kg can indicate that the stem cell preparation should be treated to deplete immunosuppressive monocytes before being administered to the patient. For example, a population of collected autologous cells can be passed through a CD14 microbead column (Mitenyi Biotec; Bergisch Gladbach, Germany) to reduce the number of monocytes in the population before the cells are returned to the patient.

Further, this document is based, at least in part, on the discovery that the ratio of natural killer (NK) cells to CD14+HLA-DR$^{DIM}$ myeloid-derived monocytic cells in a population of autologous stem cells to be infused (A-NK: A-CD14+HLA-DR$^{DIM}$), as well as the CD14+HLA-DR$^{DIM}$ cell count in a population of autologous stem cells to be infused, can be used as indicators of prognosis. For example, a patient receiving APBHSCT with an A-NK:A-CD14+ HLA-DR$^{DIM}$ less than 0.29, or a CD14+HLA-DR$^{DIM}$ count greater than or equal to $0.21 \times 10^9$ cells/kg, may have a worse prognosis than a patient receiving APBHSCT with an A-NK: A-CD14+HLA-DR$^{DIM}$ of 0.29 or greater, or a CD14+HLA-DR$^{DIM}$ count less than $0.21 \times 10^9$ cells/kg (e.g., such that the patient receiving the transplant with an A-NK:A-CD14+ HLA-DR$^{DIM}$ less than 0.29 has a lower chance of progression-free survival or overall survival than a patient receiving APBHSCT with an A-NK:A-CD14+HLA-DR$^{DIM}$ of at least 0.29). In some cases, an A-NK:A-CD14+HLA-DR$^{DIM}$ of 0.29 or less can be an indicator that the stem cell preparation should be treated to deplete monocytes or increase NK numbers prior to transfer to the patient.

Using the methods and materials provided herein can allow clinicians to identify patients who may benefit from treatment with an immunotherapeutic such as IL-15, IL-21, and/or a monocyte depleting agent. Once identified as having a ratio of lymphocytes to monocytes, a CD14+HLA-DR$^{DIM}$ count, or a ratio of NK cells to CD14+HLA-DR$^{DIM}$ cells, that suggests a poor prognosis, a patient can be administered an agent (e.g., IL-15, IL-21, and/or a monocyte depleting agent) to and improve the patient's prognosis.

In one aspect, this document features a method for treating a cancer patient, where the method includes (a) identifying the patient as having a biological sample with a LMR less than 1.0; and (b) administering to the patient a pharmaceutical composition comprising an immunotherapeutic agent. The immunotherapeutic agent can be IL-15, IL-21, or a combination of IL-15 and IL-21. The LMR can have been determined at initial diagnosis of the cancer. The patient can be a subject who was or is to be treated with APBHSCT, and the LMR can have been determined using A-ALC and A-AMC in the APBHSCT sample prior to transfer. The patient can be a subject who has received an APBHSCT, and the LMR can have been calculated using ALC and AMC in a blood sample obtained from the patient after the APBHSCT (e.g., 15 days after the APBHSCT). The patient can be a subject treated with chemotherapy, and the LMR can have been calculated using ALC and AMC within a blood sample obtained from the patient after the chemotherapy (e.g., 15 days after the chemotherapy). The chemotherapy can include treatment with one or more of cyclophosphamide, doxorubicin, vincristine, prednisone, rituximab, a combination of rituximab, cyclophosphamide, doxorubicin, vincristine, and prednisolone (RCHOP), and a combination of doxorubicin, bleomycin, vinblastine, and dacarbazine (ABVD). The cancer can be selected from the group consisting of diffuse large B-cell lymphoma, acute lymphoblastic leukemia, acute myeloid leukemia, classical Hodgkin's lymphoma, and non-Hodgkin's lymphoma, or from the group consisting of breast cancer, lung cancer, ovarian cancer, liver cancer, kidney cancer, esophageal cancer, gastric cancer, and pancreatic cancer. The can include identifying the patient as having a LMR less than 0.9, and administering a pharmaceutical composition comprising IL-15, IL-21, or a combination of IL-15 and IL-21. The method can include administering IL-15 and IL-21 simultaneously, or administering IL-15 and IL-21 separately. The method can further include conducting a positron emission tomography (PET) scan on the patient.

In another aspect, this document features a method for treating a cancer patient, where the method includes (a) identifying the patient as having a biological sample with a natural killer (NK):CD14+HLA-DR$^{DIM}$ ratio less than 0.29; and (b) administering to the patient a pharmaceutical composition comprising an immunotherapeutic agent. The immunotherapeutic agent can be IL-15, IL-21, or a combination of IL-15 and IL-21. The NK:CD14+HLA-DR$^{DIM}$ ratio can have been determined at initial diagnosis of the cancer. The patient can be a subject who was or is to be treated with APBHSCT, and the NK:CD14+HLA-DR$^{DIM}$ ratio can have been determined using absolute NK cell count and absolute CD14+HLA-DR$^{DIM}$ count in the APBHSCT sample prior to transfer. The patient can be a subject who has received an APBHSCT, and the NK:CD14+HLA-DR$^{DIM}$ ratio can have been calculated using absolute NK cell count and absolute NK cell count and absolute CD14+HLA-DR$^{DIM}$ count in a blood sample obtained from the patient after the APBHSCT (e.g., 15 days after the APBHSCT). The patient can be a subject who was treated with chemotherapy, and the NK cell count can have been calculated using absolute NK cell count and absolute NK:CD14+HLA-DR$^{DIM}$ count within a blood sample obtained from the patient after the chemotherapy (e.g., 15 days after the chemotherapy). The chemotherapy can include treatment with one or more of cyclophosphamide, doxorubicin, vincristine, prednisone, rituximab, RCHOP, and ABVD. The cancer can be selected from the group consisting of diffuse large B-cell lymphoma, acute lymphoblastic leukemia, acute myeloid leukemia, classical Hodgkin's lymphoma, and non-Hodgkin's lymphoma, or from the group consisting of breast cancer, lung cancer, ovarian cancer, liver cancer, kidney cancer, esophageal cancer, gastric cancer, and pancreatic cancer. The method can include identifying the patient as having a NK:CD14+HLA-DR$^{DIM}$ ratio less than 0.25, and administering a pharmaceutical composition comprising IL-15, IL-21, or a combination of IL-15 and IL-21. The method can include administering IL-15 and IL-21 simultaneously or separately. The method can further include conducting a PET scan on the patient.

In another aspect, this document features a method for identifying a cancer patient as having an increased likelihood of survival, where the method includes (a) determining that a biological sample containing cells from the patient has a LMR of at least 1.0 or a NK:CD14+HLA-DR$^{DIM}$ of at least 0.29; and (b) classifying the patient as having an increased likelihood of survival, as compared to a patient having a LMR less than 1.0 or a NK:CD14+HLA-DR$^{DIM}$ less than 0.29. The biological sample can contain autologous stem cells collected via an apheresis procedure. The biological sample can be a blood sample obtained from the patient before or after treatment with chemotherapy or APBHSCT. The cancer can be selected from the group consisting of diffuse large B-cell lymphoma, acute lymphoblastic leukemia, acute myeloid leukemia, classical Hodgkin's lymphoma, and non-Hodgkin's lymphoma, or from the group consisting of breast cancer, lung cancer, ovarian cancer, liver cancer, kidney cancer, esophageal cancer, gastric cancer, and pancreatic cancer. The patient can be a subject who has been treated with chemotherapy or APBHSCT, and the survival can be progression-free survival.

In still another aspect, this document features a method for identifying a cancer patient as having a decreased likelihood of survival, where the method includes (a) determining that a biological sample containing cells from the patient has a LMR less than 1.0 or a NK:CD14+HLA-DR$^{DIM}$ less than 0.29; and (b) classifying the patient as having a decreased likelihood of survival, as compared to a patient having a LMR of at least 1.0 or a NK:CD14+HLA-DR$^{DIM}$ of at least 0.29. The biological sample can contain autologous stem cells collected via an apheresis procedure. The biological sample can be a blood sample obtained from the patient before or after treatment with chemotherapy or APBHSCT. The cancer can be selected from the group consisting of diffuse large B-cell lymphoma, acute lymphoblastic leukemia, acute myeloid leukemia, classical Hodgkin's lymphoma, and non-Hodgkin's lymphoma, or from the group consisting of breast cancer, lung cancer, ovarian cancer, liver cancer, kidney cancer esophageal cancer, gastric cancer, and pancreatic cancer. The patient can be a subject who has been treated with chemotherapy or APBHSCT, and the survival can be progression-free survival.

This document also features a method for treating a population of autologous cells collected from a cancer patient, where the method includes (a) determining that the population of cells has a LMR less than 1.0 or a NK:CD14+HLA-DR$^{DIM}$ less than 0.29; and (b) contacting the population of cells with an agent that depletes monocytes. The agent can include a support coupled to CD14.

In yet another aspect, this document features a method for treating a cancer patient, where the method includes (a) identifying the patient as having a biological sample as containing an A-CD14$^+$HLA-DR$^{DIM}$ cell count that is greater than or equal to 0.21×10$^9$ cells/kg; and (b) administering to the patient a pharmaceutical composition comprising an immunotherapeutic agent. The immunotherapeutic agent can be IL-15, IL-21, or a combination of IL-15 and IL-21. The number of A-CD14$^+$HLA-DR$^{DIM}$ cells can have been determined at initial diagnosis of the cancer. The patient can be a subject who was or is to be treated by APBHSCT, where the A-CD14$^+$HLA-DR$^{DIM}$ count was determined using absolute CD14+HLA-DR$^{DIM}$ count in the APBHSCT sample prior to transfer. The patient can have received an APBHSCT, where the A-CD14$^+$HLA-DR$^{DIM}$ count was calculated using absolute CD14+HLA-DR$^{DIM}$ count in a blood sample obtained from the patient after the APBHSCT. The blood sample can have been obtained 15 days after the APBHSCT. The patient can be a subject who was treated with chemotherapy, where the LM A-CD14$^+$HLA-DR$^{DIM}$ count was calculated using absolute A-CD14$^+$HLA-DR$^{DIM}$ count within a blood sample obtained from the patient after the chemotherapy (e.g., 15 days after the chemotherapy). The chemotherapy can have included one or more of cyclophosphamide, doxorubicin, vincristine, prednisone, rituximab, RCHOP, and ABVD. The cancer can be selected from the group consisting of diffuse large B-cell lymphoma, acute lymphoblastic leukemia, acute myeloid leukemia, classical Hodgkin's lymphoma, and non-Hodgkin's lymphoma, or the group consisting of breast cancer, lung cancer, ovarian cancer, liver cancer, kidney cancer, esophageal cancer, gastric cancer, and pancreatic cancer. The method can further include conducting a PET scan on the patient.

In addition, this document features the use of a pharmaceutical composition containing an immunotherapeutic agent for treating a cancer patient, where the cancer patient is identified as having a biological sample with a LMR less than 1.0. The immunotherapeutic agent can be IL-15, IL-21, or a combination of IL-15 and IL-21. The LMR can have been determined at initial diagnosis of the cancer. The patient can be a subject who was or is to be treated by APBHSCT, where the LMR was determined using absolute lymphocyte count and absolute monocyte count in the APBHSCT sample prior to transfer. The patient can be a subject who has received an APBHSCT, where the LMR was calculated using absolute lymphocyte count and absolute monocyte count in a blood sample obtained from the patient after (e.g., 15 days after) the APBHSCT. The patient can be a subject who was treated with chemotherapy, where the LMR was calculated using absolute lymphocyte count and absolute monocyte count within a blood sample obtained from the patient after (e.g., 15 days after) the chemotherapy. The chemotherapy can include treating with one or more of cyclophosphamide, doxorubicin, vincristine, prednisone, rituximab, RCHOP, and ABVD. The cancer can be is selected from the group consisting of diffuse large B-cell lymphoma, acute lymphoblastic leukemia, acute myeloid leukemia, classical Hodgkin's lymphoma, and non-Hodgkin's lymphoma, or the group consisting of breast cancer, lung cancer, ovarian cancer, liver cancer, kidney cancer, esophageal cancer, gastric cancer, and pancreatic cancer. The patient can be identified as having a LMR less than 0.8.

In another aspect, this document features the use of a pharmaceutical composition containing an immunotherapeutic agent for treating a cancer patient identified as having a biological sample with a NK:CD14+HLA-DR$^{DIM}$ ratio less than 0.29. The immunotherapeutic agent can be IL-15, IL-21, or a combination of IL-15 and IL-21. The NK:CD14+HLA-DR$^{DIM}$ ratio can have been determined at initial diagnosis of the cancer. The patient can be a subject who was or is to be treated by APBHSCT, where the NK:CD14+HLA-DR$^{DIM}$ ratio was determined using absolute NK cell count and absolute CD14+HLA-DR$^{DIM}$ count in the APBHSCT sample prior to transfer. The patient can be a subject who has received an APBHSCT, where the NK:CD14+HLA-DR$^{DIM}$ ratio was calculated using absolute NK cell count and absolute CD14+HLA-DR$^{DIM}$ count in a blood sample obtained from the patient after (e.g., 15 days after) the APBHSCT. The patient can be a subject who was treated with chemotherapy, where the NK:CD14+HLA-DR$^{DIM}$ ratio was calculated using absolute NK cell count and absolute CD14+HLA-DR$^{DIM}$ count within a blood sample obtained from the patient after (e.g., 15 days after) the chemotherapy. The chemotherapy can include treating with one or more of cyclophosphamide, doxorubicin, vincristine, prednisone, rituximab, RCHOP, and ABVD. The cancer can be selected from the group consisting of diffuse large B-cell lymphoma, acute lymphoblastic leukemia, acute myeloid leukemia, classical Hodgkin's lymphoma, and non-Hodgkin's lymphoma, or the group consisting of breast cancer, lung cancer, ovarian cancer, liver cancer, kidney cancer, esophageal cancer, gastric cancer, and pancreatic cancer. The cancer patient can be identified as having a NK:CD14+HLA-DR$^{DIM}$ ratio less than 0.25.

In still another aspect, this document features the use of a pharmaceutical composition containing an immunotherapeutic agent for treating a cancer patient identified as having a biological sample as containing an A-CD14+HLA-DR$^{DIM}$ cell count greater than or equal to 0.21×10$^9$ cells/kg. The immunotherapeutic agent can be IL-15, IL-21, or a combination of IL-15 and IL-21. The number of A-CD14+HLA-DR$^{DIM}$ cells can have been determined at initial diagnosis of the cancer. The patient can be a subject who was or is to be treated by APBHSCT, where the A-CD14+HLA-DR$^{DIM}$ count was determined using absolute CD14+HLA-DR$^{DIM}$ count in the APBHSCT sample prior to transfer. The patient can be a subject who received an APBHSCT, where the A-CD14+HLA-DR$^{DIM}$ count was calculated using absolute CD14+HLA-DR$^{DIM}$ count in a blood sample obtained from the patient after (e.g., 15 days after) the APBHSCT. The patient can be a subject who was treated with chemotherapy, where the LM A-CD14+HLA-DR$^{DIM}$ count was calculated using absolute A-CD14+HLA-DR$^{DIM}$ count within a blood sample obtained from the patient after (e.g., 15 days after) the chemotherapy. The chemotherapy can include treating with one or more of cyclophosphamide, doxorubicin, vincristine, prednisone, rituximab, RCHOP, and ABVD. The cancer can be selected from the group consisting of diffuse large B-cell lymphoma, acute lymphoblastic leukemia, acute myeloid leukemia, classical Hodgkin's lymphoma, and non-Hodgkin's lymphoma, or selected from the group consisting of breast cancer, lung cancer, ovarian cancer, liver cancer, kidney cancer, esophageal cancer, gastric cancer, and pancreatic cancer.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A, autograft lymphocytes were gated on a forward scatter (FSC)/side scatter (SSC) plot. FIG. 2B, autograft natural killer cells (CD16$^+$, CD56$^+$, CD3$^-$) were enumerated from the lymphocyte-positive gate. FIG. 2C, autograft monocytes were gated on a FSC/SSC plot. FIG. 2D, autograft monocytes were further gated to determine CD14+ cells. FIG. 2E, autograft CD14+ HLA-DR$^{DIM}$ were enumerated from the CD14+ gate.

FIG. 3A, ROC and AUC for A-NK:A-CD14+HLA-DR$^{DIM}$≥0.29 with an AUC=0.75, 95% CI, 0.70-0.80, P<0.0003. FIG. 3B, K-fold cross-validation ROC and AUC for A-NK:A-CD14+HLA-DR$^{DIM}$ with an AUC=0.76, 95% CI, 0.70-0.82.

FIGS. 4A-4D are a series of Kaplan-Meier plots showing OS or PFS for non-Hodgkin lymphoma patients treated with APBHSCT using various populations of autologous cells. FIG. 4A, OS for A-CD14+HLA-DR$^{DIM}$<0.21×10$^9$ cells/kg vs. A-CD14+HLA-DR$^{DIM}$≥0.21×10$^9$ cells/kg. FIG. 4B, PFS for A-CD14+HLA-DR$^{DIM}$<0.21×10$^9$ cells/kg vs. A-CD14+ HLA-DR$^{DIM}$≥0.21×10$^9$ cells/kg. FIG. 4C, OS for A-NK:A-CD14+HLA-DR$^{DIM}$ ratio≥0.29 vs. A-NK:A-CD14+HLA-DR$^{DIM}$ ratio<0.29. FIG. 4D, PFS for A-NK:A-CD14+HLA-DR$^{DIM}$ ratio≥0.29 vs. A-NK:A-CD14+HLA-DR$^{DIM}$ ratio<0.29.

DETAILED DESCRIPTION

Figure 1A:
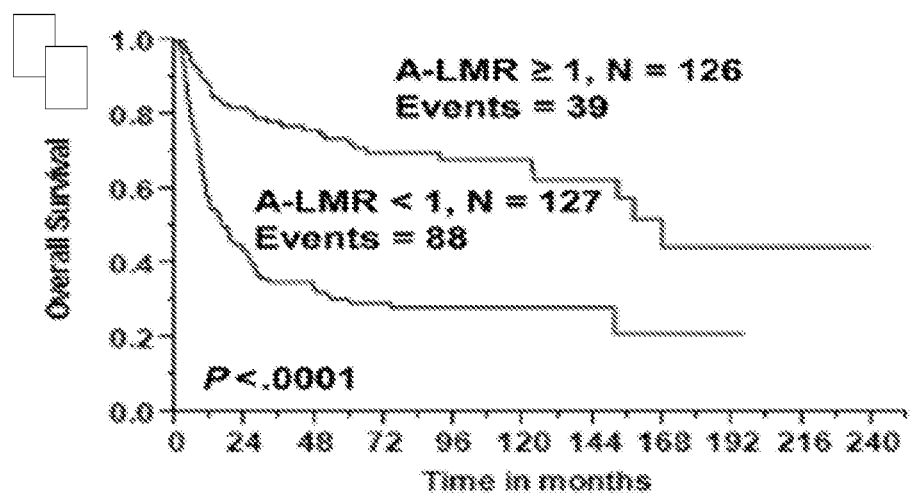
FIGS. 1A and 1B are a series of Kaplan-Meier plots showing overall survival (top), progression-free survival (middle), and lymphoma-specific survival (bottom) for DLBCL patients treated with APBHSCT, using a population of autologous cells having an A-LMR of 1 or greater, or less than 1, as indicated.
Figure 1A:
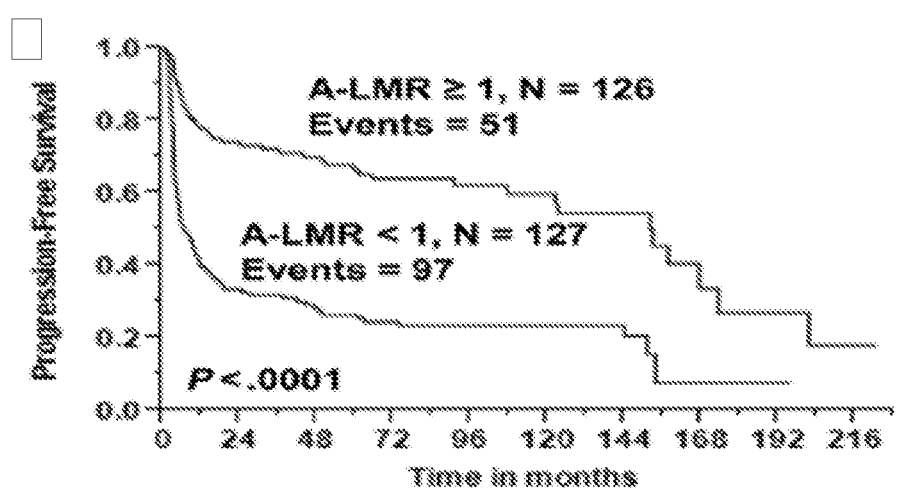
Figure 1A:
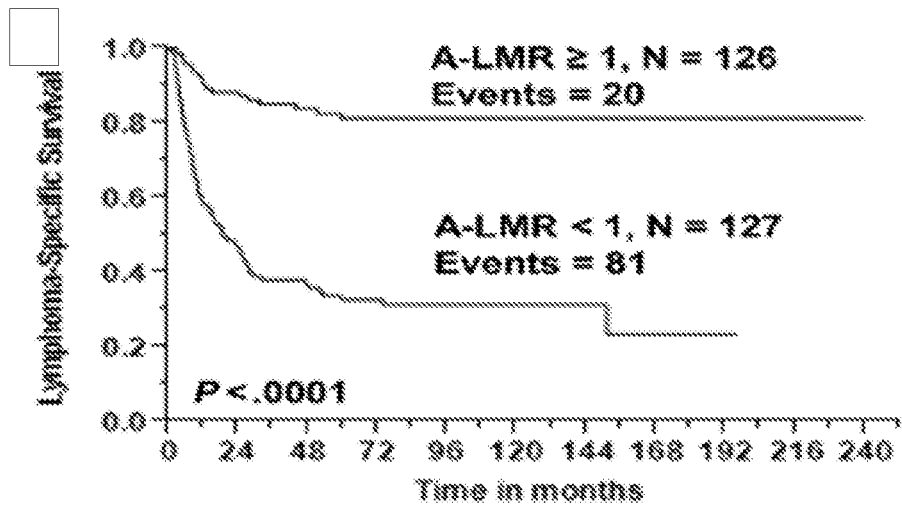

This document provides materials and methods that for treating cancer patients, and is based, at least in part, on the discoveries that A-LMR and LMR, as well as A-AMC, AMC, and A-NK:A-CD14+HLA-DR$^{DIM}$, can be powerful indicators of cancer patient prognosis. Thus, this document provides materials and methods for obtaining a population of stem cells and/or treating a patient to achieve an A-LMR or a LMR of at least 1.0, as well as materials and methods for obtaining a population of stem cells and/or treating a patient to achieve an A-NK:A-CD14+HLA-DR$^{DIM}$ or NK:CD14+HLA-DR$^{DIM}$ of at least 0.29.

In some embodiments, a subject treated according to the methods described herein can be a human cancer patient diagnosed with, for example, non-Hodgkin lymphoma, Hodgkin's disease, classical Hodgkin lymphoma, multiple myeloma, acute myeloid leukemia, diffuse large B-cell lymphoma, or acute lymphoblastic leukemia, or a solid tumor such as a breast tumor, lung tumor, ovarian tumor, liver tumor, or kidney tumor. The methods provided herein can include the step of returning a population of collected autologous cells to the patient. The cell population can be returned to the patient by, for example, intravenous infusion or any other suitable method known in the art. In some embodiments, the patient can be in remission from the cancer, either prior to collection of the cells or prior to returning the cells to the patient.

As used herein, "autologous" as it relates to transplantation refers to a graft in which the donor and recipient is the same individual. Thus, in an autologous transplant cells are harvested from a subject and then returned to the same subject. In contrast, an "allogeneic" transplant refers to a graft in which the donor and recipient are genetically non-identical individuals from the same species. A "xenogeneic" transplant refers to a graft in which the donor and recipient are of different species.

As used herein, an APBHSCT refers to a procedure in which a sample of a subject's own stem cells are removed and subsequently transplanted back into the same subject. Stem cells can be harvested from bone marrow (BM) or peripheral blood (PB), for example. Once obtained, stem cells can be frozen until needed. For example, stem cells can be obtained from a patient, cryopreserved at temperatures ≤–85° C., and then thawed and returned (i.e., transplanted, typically by transfusion) to the patient. In some embodiments, stem cell aliquots can be thawed, loaded into one or more sterile syringes or infusion bags, and injected intravenously over a period of time ranging from about 30 minutes to about 45 minutes.

In some embodiments, stem cells capable of reconstituting a patient's immune system can be obtained from the patient's peripheral circulation following mobilization of such cells from BM into PB. Mobilization of stem cells can be accomplished by treatment of a patient with one or more factors that can (i) stimulate an increase in proliferation of stem cells and/or progenitor cells, and/or (ii) stimulate migration of stem cells and/or progenitor cells from the BM into the peripheral circulation. Such factors can be administered with adjuvants and/or other accessory substances, separately or in combination as desired. Examples of factors that can be used in this aspect include, without limitation, granulocyte colony-stimulating factor (G-CSF), granulocyte/macrophage colony-stimulating factor (GM-CSF), c-kit ligand (stem cell factor (SCF)), interleukin-2, -7, -8, and -12 (IL-2, IL-7, IL-8, and IL-12), and flt-3 ligand. See, e.g., Bungart et al. (1990) *Br. J. Haematol.* 76:174; Terella et al. (1993) *Bone Marrow Transplant.* 11:271; Molineux et al. (1991) *Blood* 85:275; Grzegorzewski et al. (1994) *Blood* 83:377; Laterveer et al. (1995) *Blood* 85:2269; Jackson et al. (1995) *Blood* 85:2371; and Lyman et al. (1994) *Blood* 83:2795. Factors to be administered can include, for example, G-CSF alone (e.g., 10 µg/kg/day G-CSF), G-CSF+flt-3 ligand (e.g., 10 µg/kg/day G-CSF+50 µg/kg/day flt-3 ligand), or GM-CSF+flt-3 ligand (e.g., 5 µg/kg/day GM-CSF+50 µg/kg/day flt-3 ligand). See, e.g., Sudo et al. (1997) *Blood* 89:3186. Such factors can be administered prior to harvest or starting on the day of harvest, for example, and can be given on a daily basis for one to seven days (e.g., for one, two, three, four, five, six, or seven days), or until stem cell harvesting is complete. Factors that stimulate stem cell proliferation or mobilization can be administered using any suitable method. Typically, such factors can be administered parenterally (e.g., by subcutaneous, intrathecal, intraventricular, intramuscular, or intraperitoneal injection, or by intravenous drip). Mobilization of stem cells with, for example, GM-CSF and flt-3 ligand can be evaluated by determining the number of CD34+ cells present before, during, and/or after treatment with one or more mobilizing agents. In some embodiments, the number of CD34+ cells can be determined by FACS analysis using CD34-specific antibodies conjugated to fluorescent or other labeling moieties.

Following or during mobilization, peripheral blood stem cells (PBSC) can be collected using, for example, an apheresis procedure. The process of apheresis, which is well known in the art, involves removal of whole blood from a patient or donor. Within an instrument that is essentially designed as a centrifuge, the components of the whole blood are separated. One or more of the separated portions is then withdrawn, and the remaining components can be retransfused into the patient or donor. Thus, for example, all or most (e.g., 80%, 90%, 95%, 99%, or 100%) of the erythrocytes in a sample of whole blood can be returned to a patient during an apheresis procedure, while lymphocytes (e.g., NK cells) and stem cells can be collected. Apheresis can be performed as many as four times per week (e.g., one, two, three, or four times per week). In some embodiments, a commercially available blood cell collection device can be used, such as the CS3000® blood cell collection device or the Fenwal Amicus collection device, both of which are marketed by the Fenwal Division of Baxter Healthcare Corporation (Fenwal Laboratories, Deerfield, Ill.). Methods for performing apheresis with these machines are described in Williams et al. (1990) *Bone Marrow Transplantation* 5:129-133; Hillyer et al. (1993) *Transfusion* 33:316-321; and Porrata et al. (2016) *Biol Blood Marrow Transplant* 22:1017-1023, for example, all of which are incorporated herein by reference in their entirety.

In some embodiments, a total blood volume between 9.5 and 10 L per apheresis procedure can be processed at a flow rate of 50 to 90 mL/min. Following collection, a cell count can be performed on an aliquot of the total product to determine the number of stem cells. Cells can be collected until the total sample taken from the patient reaches a concentration of at least $2 \times 10^6$ CD34$^+$ stem cells/kg (e.g., $2 \times 10^6$ CD34$^+$ cell/kg to $3 \times 10^6$ CD34$^+$ cells/kg, $2 \times 10^6$ CD34$^+$ cell/kg to $2.5 \times 10^6$ CD34$^+$ cells/kg, or $2.5 \times 10^6$ CD34$^+$ cell/kg to $3 \times 10^6$ CD34$^+$ cells/kg).

Despite various methods of PBSC mobilization, adequate numbers of PBSC for APBHSCT may be not collected from some patients during a single apheresis procedure. In these patients, BM harvest or a second attempt at PBSC mobilization can be performed. Alternatively, these patients may be excluded from proceeding to APBHSCT.

Apheresis products can be centrifuged (e.g., at 400 g for 10 minutes), and the plasma can be removed to yield a total volume of, for example, about 100 mL. The resulting cell suspension can be mixed with a physiological freezing solution [e.g., 100 mL minimal essential medium such as MEM-S (Invitrogen Life Technologies, Carlsbad, Calif.) supplemented with 20% dimethylsulfoxide (DMSO)]. Cell/media suspensions can be transferred to freezing bags (such as those manufactured by Delmed, Canton, Mass.) or any other freezing receptacle known in the art, and frozen to −100° C. using, for example, a computer-controlled cryopreservation device (e.g., the Cryoson-BV-6; Cryoson Deutschland GmbH, FRG). The cells then can be transferred into liquid nitrogen and stored at until transplantation.

Patients typically undergo a pre-transplant workup to evaluate, for example, heart, liver, kidney, and lung function, as well as current disease status. In some embodiments, patients deemed to be eligible (e.g., healthy enough) for APBHSCT are subjected to a tumor debulking procedure prior to APBHSCT. For example, a patient can be treated with high doses of chemotherapy, radiation therapy, and/or surgery (e.g., surgery with anesthesia) before the transplant. Stem cells for transplant typically are collected prior to tumor debulking regimens, since such potentially lethal procedures can be immunosuppressive and can severely damage or destroy the BM. APBHSCT following a debulking procedure can reconstitute the patient's immune cells with stem cells present in the transplant.

In some embodiments, a patient's stem cells can be collected by BM harvest using procedures known in the art, or by a stem cell apheresis procedure as described above, for example. Collected stem cells can be cryopreserved, and the patient can undergo a debulking procedure such as high-dose chemotherapy and/or radiation therapy. After the debulking procedure is completed, the patient's stem cells can be transplanted. APBHSCT can be done almost immediately after a debulking procedure (e.g., 24 to 48 hours after HDT). Alternatively, a longer period of time (e.g., a week to several months) can elapse between a debulking procedure and APBHSCT. Due to the likelihood of immunosuppression as a result of the debulking procedure, protective isolation precautions generally are taken after APBHSCT at least until the reinfused stem cells begin to engraft. "Engraftment" refers to a process whereby the transplanted stem cells begin to differentiate into mature blood cells. In addition, stem cells can be treated prior to transplantation with, for example, anticancer drugs or antibodies to reduce the number of cancerous cells that may be present in the sample. Such procedures are referred to as "purging."

In some embodiments of the methods provided herein, subjects (e.g., cancer patients) can be treated by administration of autologous cell populations that contain stem cells and other cell types, including, for example, red blood cells (RBC), lymphocytes, and monocytes. Lymphocytes are white blood cells (WBC) that are formed in lymphatic tissue throughout the human body (e.g., lymph nodes, spleen, thymus, tonsils, Peyer's Patches, and bone marrow). In normal adults, lymphocytes comprise approximately 22% to 28% of the total number of leukocytes in the circulating blood. As used herein, the term "lymphocyte" includes NK cells, B cells, and T cells (e.g., T helper cells, cytotoxic T cells, and T suppressor cells). NK cells are directly cytotoxic to foreign cells (e.g., foreign cancer cells), and do not require complement activity to effect their lysis. NK cells represent the body's first line of defense against malignancy. B cells produce immunoglobulins, and T cells are involved in modulation of immune responses and in regulation of erythropoiesis. Different types of lymphocytes can be distinguished from each other and from other cell types based on the cell type-specific expression of particular molecular markers, generally cell surface markers. For example, NK cells bear on their surface CD16 and/or CD56 markers. B cells bear at least one of the cell surface markers CD19 and CD20. T cells bear one or more of the cell surface markers CD3, CD4, and CD8. Typically, cytotoxic T cells express CD8, whereas helper T cells express CD4.

As used herein, the term "absolute lymphocyte count" (ALC) refers to the total number of lymphocytes per unit of whole blood or blood cells in a sample or in a subject (e.g., a human patient). A unit can be, for example, a liter (L), milliliter (mL), or microliter (μL). Typically, but not always, ALC is measured as the number of mature lymphocytes per μL of blood, and includes the cumulative numbers of B cells, T cells, and NK cells. Stem cells, lymphocyte precursor cells, and lymphocyte progenitor cells typically are not included in the ALC. Stem cells can be differentiated from lymphocytes in that stem cells express the cell surface marker CD34, whereas mature lymphocytes do not. Moreover, lymphocytes express specific cell surface markers as described above (NK cells: CD16 and/or CD56; B cells: CD20 and/or CD19; T cells: CD3, CD4, and/or CD8), whereas stem cells do not express these markers.

To determine an ALC, a sample of blood can be collected from a patient. For example, blood can be collected in a rubber-stopped tube containing EDTA or another medically acceptable anti-coagulant. Blood can be collected using any route of entry to the circulatory system known in the art. The blood sample then can be analyzed to determine the ALC. In some embodiments, an ALC can be obtained using an automated system for counting blood cells in a sample. Such cell counting systems typically are based on a principle by which unstained, unlabeled cells are sorted and counted based on morphological characteristics including, without limitation, cell size, cell shape, nuclear size, and nuclear shape. For example, the GEN-S™ Hematology Analyzer identifies and counts cell types based on three general criteria: volume, conductivity, and scatter (see U.S. Pat. No. 5,125,737). A blood sample can be treated before analysis with reagents and/or physical agitation to lyse the RBC, thereby leaving WBC for analysis. The Gen-S™ Analyzer uses a process of DC impedance by which the cells are collided with light to physically measure the volume displaced by the entire cell in an isotonic diluent. Cell size thus can be accurately determined regardless of the orientation of the cell in the light path. Cells can be further collided with an alternating current in the radio frequency range that can permeate cell membranes, such that information can be obtained with regard to internal structure including, for example, chemical composition and nuclear structure. A cell can be collided with a laser beam that, upon contacting the cell, scatters and spreads out in all directions, generating median angle light scatter signals. These signals can be collected to yield information regarding cellular granularity, nuclear lobularity, and cell surface structure. Thus, such a system can count and differentiate RBC from WBC based on the presence or absence of a nucleus, and can count and differentiate the different types of WBC based on the ratio of nuclear to cytoplasmic volume, lobularity of the nucleus, and granularity of the cytoplasm as described below, for example.

ALC also can be determined by placing a known volume of a blood sample onto a glass microscope slide, smearing the sample to create a thin film of blood on the slide, and staining the sample using standard histological stains such as, for example, hematoxylin and eosin (H & E). Briefly, a blood smear can be dried and subsequently fixed onto a slide using a fixative such as, without limitation, neutral buffered formalin, formaldehyde, paraformaldehyde, glutaraldehyde, Bouin's solution, mercuric chloride, or zinc formalin. The slides then can be immersed in a solution of Harris Hematoxylin, rinsed in water, immersed in a solution of Eosin, rinsed in water, dehydrated in ascending alcohol solutions, and cleared in xylenes. In blood smears that have been stained using H & E, nuclei and other basophilic structures stain blue, whereas cytoplasm and other acidophilic structures stain light to dark red (Sheehan et al. (1987) *Theory and Practice of Histotechnology*, 2nd Edition, Battelle Memorial Institute, Columbus, Ohio), which is incorporated herein by reference in its entirety. The number of lymphocytes present in a blood smear can be counted based on lymphocytic morphological criteria accepted in the art.

For example, when stained with H & E, the lymphocyte nucleus is deeply colored (purple-blue) and is composed of dense aggregates of chromatin within a sharply defined nuclear membrane. The nucleus generally is round, eccentrically located, and surrounded by a small amount of light blue staining cytoplasm. The volume of nucleus to cytoplasm in a lymphocyte typically is about 1:1.2. Lymphocytes can be differentiated from RBC in that RBC have no nuclei. Lymphocytes can be differentiated from neutrophils in that neutrophils have nuclei with 2 to 5 lobes, while lymphocyte nuclei are not lobed. Lymphocytes can be differentiated from basophils and eosinophils in that those cells have cytoplasmic granules, while lymphocytes do not have cytoplasmic granules. Lymphocytes can be differentiated from monocytes in that monocytes are 16 to 20 µm in diameter, while lymphocytes are 7 to 10 µm in diameter. In addition, one of skill in the art may refer to any of a number of hematology or histological texts or atlases (e.g., Wheater et al. (1987) *Functional Histology* 2nd Ed. Churchill Livingstone, incorporated herein by reference in its entirety) to determine the physical appearance of a lymphocyte.

ALC also can be determined by immunolabeling lymphocytes with antibodies specific for lymphocyte cell surface markers, and counting the immunolabeled cells using fluorescence flow cytometry (FFC). For example, NK cells can be labeled with one or more fluorescently labeled antibodies specific for CD16 and/or CD56. Similarly, B cells can be labeled with one or more fluorescently labeled antibodies specific for the adhesion molecules CD20 and/or CD19, and T cells can be labeled with one or more fluorescently labeled antibodies specific for CD3, CD4, and/or CD8, and. To determine ALC, cell surface marker-specific antibodies can be labeled with the same fluorophore (e.g., Cy-5, fluorescein, or Texas Red). In a FFC procedure, individual cells are held within a thin stream of fluid and passed through one or more laser beams, one cell at a time, causing light to scatter and the fluorescent dyes to emit light at various predetermined frequencies. Photomultiplier tubes convert the light to electrical signals, allowing for quantitation of the number of cells bearing the fluorophore. If all lymphocyte subtypes are labeled with the same fluorophore, quantification of the number of fluorophore-bearing cells will yield an ALC. FFC and quantitation is further described in, for example, U.S. Pat. No. 4,499,052. In addition, a FFC machine can be adapted for fluorescence activated cell sorting (FACS), i.e., the separation (and collection) of (a) fluorescent cells from non-fluorescent cells; (b) strongly fluorescent cells from weakly fluorescent cells; or (c) cells fluorescing at one wavelength from cells fluorescing at another wavelength.

Monocytes are large phagocytic WBC that have a simple nucleus and clear, grayish cytoplasm. Monocytes can differentiate into macrophages and myeloid lineage dendritic cells. Classical monocytes are characterized by high level expression of the CD14 cell surface receptor without expression of the CD16 cell surface receptor, but other populations of monocytes are characterized by low level expression of CD14 and high level expression of CD16, or high level expression of CD14 and low level expression of CD16.

The term "absolute monocyte count" (AMC) refers to the total number of mature monocytes per unit of whole blood or blood cells in a sample or in a subject (e.g., a human patient). Again, a unit can be, for example, a L, mL, or µL. AMC can be determined by, for example, using an automated cell count machine or flow cytometry, as described above with regard to ALC.

Once ALC and AMC have been determined, whether the A-ALC and A-AMC in a population of collected stem cells from a patient, or the ALC and AMC in a blood sample obtained from a subject, the ratio of lymphocytes to monocytes can be determined. The ratio of A-ALC to A-AMC for a population of autologous cells to be used in APBHSCT is referred to herein as A-LMR, while the ratio of ALC to AMC in a biological sample (e.g., a blood sample) collected from a subject is referred to herein as LMR. An A-LMR for a population of collected autologous stem cells that is at least 1.0 (e.g., 1.1, 1.2, 1.3, 1.4, 1.5, 2.0, 2.5, or greater than 2.5) can indicate that the patient receiving the APBHSCT has a greater likelihood of progression-free and overall survival than he/she would if the A-LMR was less than 1.0 (e.g., 0.9, 0.8, 0.7, 0.6, 0.5, or less than 0.5). Further, a LMR of at least 1.0 determined for a biological sample (e.g., a blood sample) obtained from a cancer patient at diagnosis, before or after chemotherapy, or from an APBHSCT recipient after transplant (e.g., 15, 30, 60, or 90 days post-transplant) can indicate that the patient has a greater likelihood of progression-free and overall survival than he/she would if the LMR was less than 1.0.

This document also provides methods for assessing a patient's prognosis based on the ratio of NK cells to CD14+ HLA-DR$^{DIM}$ monocytes in a biological (e.g., blood) sample from the patient, or in a population of collected autologous stem cells to be transferred back to the patient. NK cells can be collected using an apheresis procedure as described above. In some embodiments, the number of collected NK cells can be monitored. For example, the number of NK cells can be determined at one or more points during collection of the sample from the patient. The number of NK cells also can be determined after completion of a collection. Once the population of total collected cells includes at least about $0.5 \times 10^9$ NK cells/kg, they can be returned to the patient. The number of collected CD14+HLA-DR$^{DIM}$ cells also can be determined, and the ratio as compared to NK cells can be determined. The number of collected NK cells and CD14+ HLA-DR$^{DIM}$ cells can be monitored using methods such as those described above. In some embodiments, the number of collected NK cells can be determined using immunolabeling with one or more fluorescently labeled antibodies specific for CD16 and/or CD56, and counting with FACS, while the number of collected CD14+HLA-DR$^{DIM}$ cells can be determined using immunolabeling with one or more labeled antibodies specific for CD14 and/or HLA-DR$^{DIM}$, followed by counting with FACS.

Once the numbers of NK cells and CD+HLA-DR$^{DIM}$ cells have been determined, whether the A-NK and A-CD14+ HLA-DR$^{DIM}$ in a population of collected autologous cells to be used for APBHSCT, or the NKC and CD14+HLA-DR$^{DIM}$ in a blood sample obtained from a subject, the ratio of NK cells to CD14+HLA-DR$^{DIM}$ cells can be determined. A ratio of NK:CD14+HLA-DR$^{DIM}$ that is at least 0.29 (e.g., 0.30, 0.35, 0.40, 0.45, or more than 0.45) can indicate that the patient receiving the stem cells via APBHSCT has a greater likelihood of progression-free and overall survival than he/she would if the ratio was less than 0.29 (e.g., 0.28, 0.25, 0.23, 0.20, or less than 0.20). Further, a NK:CD14+HLA-DR$^{DIM}$ of at least 0.29 determined for a biological sample (e.g., a blood sample) obtained from a cancer patient at diagnosis, before or after chemotherapy, or from an APBHSCT recipient, post-transplant (e.g., 15, 30, 60, or 90 days post-transplant) can indicate that the patient has a greater likelihood of progression-free and overall survival than he/she would if the NK:CD14+HLA-DR$^{DIM}$ ratio was less than 0.29.

The methods provided herein also can include treatment of a patient or a cell population (e.g., in a biological sample such as an apheresis product) with one or more agents that stimulate proliferation, maturation, differentiation, function, and/or activity of immune cells (e.g., lymphocytes, including NK cells). For example, a patient or a population of collected cells can be contacted with an agent such as IL-2, IL-12, IL-15, IL-17, IL-21, interferon alpha (IFN-α), or interferon gamma (IFN-γ). These agents can be native factors obtained from a natural source, factors produced by recombinant DNA methodology, chemically synthesized polypeptides or molecules, or any derivative having the functional activity of the native factor. Since agents such as these can enhance the number and/or activity of lymphocytes (e.g., NK cells), a patient may be subjected to shorter or fewer apheresis procedures in order to harvest a cell population containing, for example, an A-LMR or LMR of at least 1.0, and/or an A-NK:A-CD14+HLA-DR$^{DIM}$ of at least 0.29.

In some embodiments, a population of collected cells can be contacted with an agent or platform that depletes monocytes. In some cases, the population of cells may be identified as having an A-LMR or LMR less than 1.0, or an A-NK:A-CD14+HLA-DR$^{DIM}$ or NK:CD14+HLA-DR$^{DIM}$ less than 0.29. Suitable methods for depleting monocytes include, for example, contacting a population of cells with a support (e.g., a solid surface such as a bead) coupled to CD14 (e.g., CD14 microbeads; Mitenyi Biotec), and collecting the cells that do not bind to the support.

In some embodiments, a population of cells (e.g., a population of collected autologous lymphocytes containing NK cells and monocytes) can be contacted in vitro with one or more agents such as those listed above. For example, collected cells can be placed in a vessel (e.g., a bag, a tube, a vial, or any other suitable container) and contacted with one or more agents such as those described above. In some embodiments, cells can be contacted in vitro with IL-2 at a dose of, for example, about $1.5 \times 10^6$ to about $2.0 \times 10^6$ units. Lymphocyte (e.g., NK cell) enhancing agents can be added to cells within a container such as a bag (e.g., a blood bag), tube, or vial, or such a vessel can contain one or more such agents prior to placement of cells within the vessel. In some embodiments, one or more agents can be dispersed on an inner surface of the vessel. For example, an agent in liquid form can be dispersed (e.g., sprayed) onto an inner surface of the vessel and allowed to dry. Alternatively, an agent in solid (e.g., lyophilized or powdered) form can be dispersed on an inner surface of the vessel. In another alternative, an agent in liquid or solid form can simply be placed within the vessel.

Alternatively, one or more lymphocyte enhancing agents can be administered to a patient. A patient can be treated with such an agent prior to collection of a biological sample containing lymphocytes and monocytes, or a patient can be treated post-APBHSCT. For example, the number of NK cells in the PB of a patient can be monitored following APBHSCT, and a NK cell enhancing agent can be administered to the patient if the number of NK cells is below a particular threshold at a particular time point (e.g., at post-transplant day 15). A suitable threshold can be, for example, about 80 NK cells/µL of blood (e.g., about 75 NK cells/µL or about 85 NK cells/µL). Similarly, a NK cell enhancing agent can be administered to a patient post-APBHSCT if the ALC-15 is less than 500 cells/µL of blood. Agents such as those listed above can be administered to a patient via any pharmaceutically acceptable route known in the art, including, for example, intravenous injection, intra-arterial injection, subcutaneous injection, intramuscular injection, intraperitoneal injection, or oral administration in the form of a tablet, capsule, or syrup. In some embodiments, IL-2 can be administered to a patient prior to collection of autologous cells, or after APBHSCT. In another embodiment, a patient can be treated with IFN-γ at a concentration of, for example, between about $1 \times 10^5$ and about $1 \times 10^7$ units/m$^2$. When the treatment is post-APBHSCT, the agent(s) can be administered from the day of transplant up to about 21 days following the transplant.

In some embodiments, patients or collected cell populations (e.g., populations containing lymphocytes and monocytes) also can be treated with one or more agents that activate the T cell signal transduction pathway, leading to lymphocyte activation. A T cell activator can be, without limitation, one or more of the following: IL-1, IL-2, IL-4, IL-5, IL-6, IL-7, IL-12, IL-13, IFNα, IFNγ, tumor necrosis factor (TNFα), an anti-CD3 antibody or antigen-binding fragments thereof (anti-CD3), an anti-CD28 antibody or antigen-binding fragments thereof (anti-CD28), phytohemagglutinin, concanavalin-A, and phorbol esters. As above, these agents can be native factors obtained from a natural source, factors produced by recombinant DNA methodology, chemically synthesized polypeptides or molecules, or any derivative having the functional activity of the native factor.

The invention will be further described in the following examples, which do not limit the scope of the invention described in the claims.

EXAMPLES

Example 1—A-LMR as a Predictor of Survival

Figure 1B:
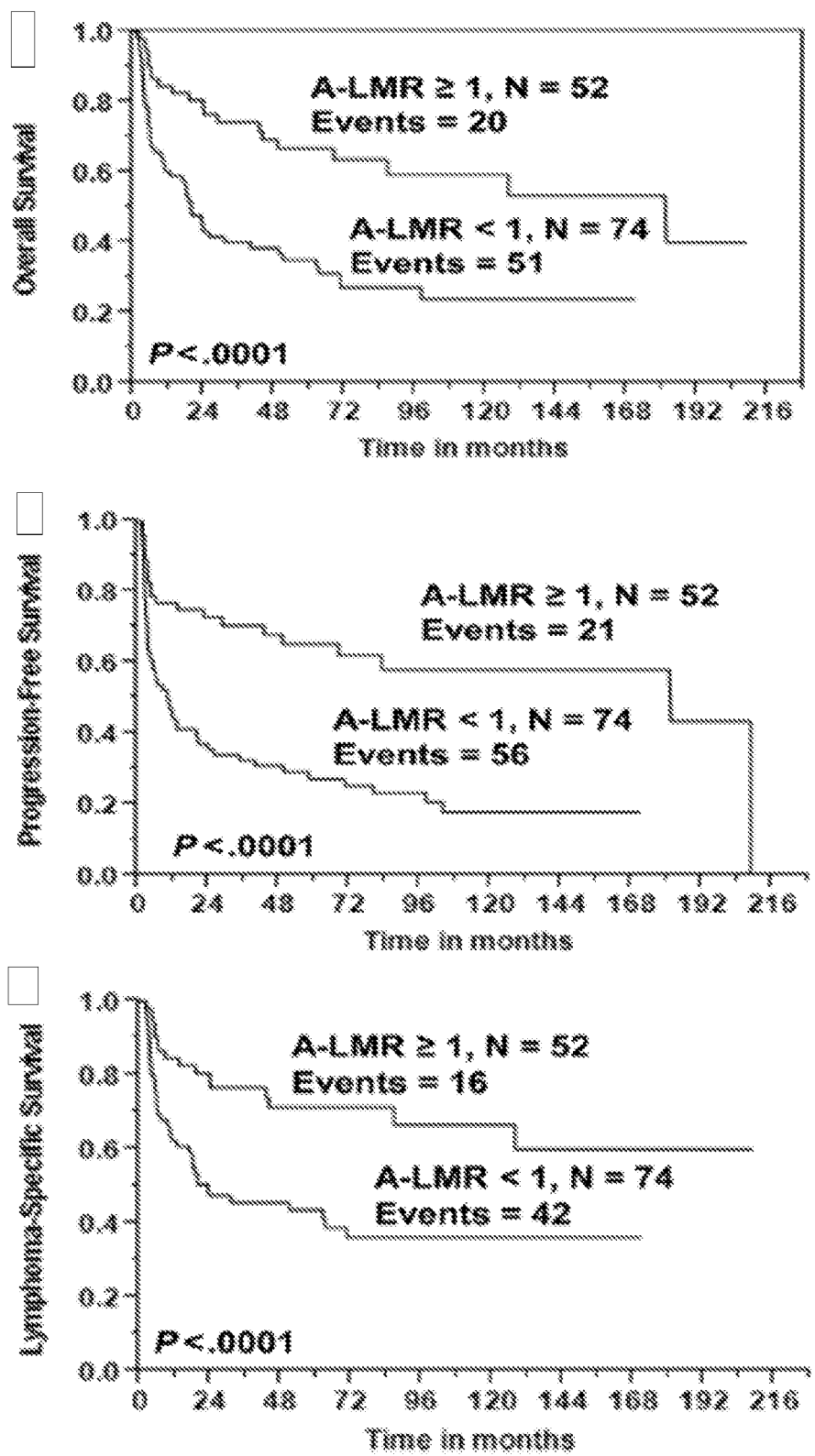

Retrospective studies were conducted to determine whether the A-LMR for autologous cells infused into DLBCL patients during APBHSCT could be correlated to survival. In a training set including 253 patients, and also in a validation set containing 126 patients, an A-LMR of 1 or higher correlated with increased overall survival (FIGS. 1A and 1B, top panels), increased progression-free survival (FIGS. 1A and 1B, middle graphs), and increased lymphoma-specific survival (FIGS. 1A and 1B, bottom graphs), while an A-LMR less than 1 correlated with decreased overall survival (FIGS. 1A and 1B, top panels), decreased progression-free survival (FIGS. 1A and 1B, middle graphs), and decreased lymphoma-specific survival (FIGS. 1A and 1B, bottom graphs). Details of these studies are provided elsewhere (Porrata et al. (2014) Biol Blood Marrow Transplant 20:1804-1812).

Example 2—A-NK:A-CD14+HLA-DR$^{DIM}$ as a Predictor of Survival

A double-blind, phase III, randomized clinical trial was conducted to determine whether A-NK:A-CD14+HLA-DR$^{DIM}$ can be used as a predictor of survival in 111 non-Hodgkin's lymphoma (NHL) patients. The primary end point of was to assess the impact of A-NKC/ACD14$^+$HLA-DR$^{DIM}$ ratio on overall survival (OS) and progression-free survival (PFS). A secondary end point was to determine whether the A-NKC/A-CD14$^+$HLA-DR$^{DIM}$ ratio is an independent prognostic factor for OS and PFS.

The prognostic factors evaluated in this study included: international prognostic index (IPI; "The International Non-Hodgkin's Lymphoma Prognostic Factors Project. A predictive model for aggressive non-Hodgkin's lymphoma," N Engl J Med 1993, 329:987-994) at diagnosis ($\geq 2$), age at diagnosis ($\leq 60$ vs. $>60$ years), lactate dehydrogenase (LDH) at diagnosis ($>$normal), ECOG (Eastern Cooperative Oncology Group) performance status at diagnosis ($>1$ vs. $\leq 1$), extranodal sites at diagnosis ($>1$ versus $\leq 1$), stage at diagnosis (III/IV vs. I/II), histologies at diagnosis (DLBCL vs. others), disease status before APBHSCT (complete response vs. partial response), infused CD34$^+$ cell count, Plerixafor use, and A-NKC/A-CD14$^+$HLA-DR$^{DIM}$ ratio. Basic characteristics of the study participants are shown in TABLE 1. Further details of these studies are described elsewhere (Porrata et al. 2016, supra; and Kansagra et al. 2018, Bone Marrow Transplantation 53:146-154).

The double-blind, randomized, phase III clinical trial was designed to assess whether the PFS was significantly increased among those patients whose apheresis was done using a modification to a standard Fenwal Amicus setting where the mononuclear cell offset=1.5 and RBC=6.0, compared with settings where mononuclear cells=1.5 and RBC=5.0.

For stem cell mobilization, patients received 10 µg/kg of G-CSF subcutaneously (SC) daily for 5 to 7 consecutive days alone or in conjunction with 0.24 mg/kg of Plerixafor for up to 4 consecutive days by SC injection. Patients started with G-CSF and after 4 days of treatment, if the peripheral blood CD34$^+$ count was $\geq 10$ cells/µL, stem cell collection began. If the peripheral blood CD34$^+$ count was $<10$ cells/µL, Plerixafor was added that evening and collections were initiated the next day. Apheresis collections were to be performed daily, with a goal of at least $2 \times 10^6$ CD34$^+$ cells/kg. Additional collections were at the discretion of the transplantation team. Patients who failed mobilization or did not collect at least $2 \times 10^6$ CD34$^+$ cells/kg were allowed to choose to either undergo a second mobilization/apheresis or discontinue study participation.

For conditioning, all patients received BEAM chemotherapy: BCNU (carmustine, 300 mg/m$^2$) on day −6, Etoposide (100 mg/m$^2$) twice daily from days −5 to −2, ARA-C (Cytarabine, 100 mg/m$^2$) twice daily from days −5 to −2, and Melphalan (140 mg/m$^2$) on day −1.

OS was measured from the date of APBHSCT to the date of death or last follow-up, and PFS was defined as the time from APBHSCT to time of progression, relapse, death or last follow-up (Cheson et al. 2007, J Clin Oncol 25:579-586).

Previously frozen autograft mononuclear cells (0.5-1.0×10$^6$ cells/mL) were thawed and aliquoted into 96-well round-bottomed plates (100 mL/well). The following monoclonal antibodies were used for autograft mononuclear cell immunophenotyping by flow cytometry: anti-human CD3 FITC, anti-human CD16 phycoerythrin (PE), and anti-human CD56 PE for NK cells, and anti-human CD14 FITC and anti-human HLA-DR PE-cyanin 5.5 (PE-Cy5.5) for HLA-DR dim monocytes (BD Pharmingen; San Jose, Calif.). The desired antibody or antibody pool was added at 5 µL of each antibody/well. The cells and antibodies were incubated for 30 minutes at 4° C. and washed twice with 1×PBS (Cellgro; Manassas, Va.), 0.1% BSA and 0.05% sodium azide (Sigma; St Louis, Mo.). Three-color flow cytometry was performed on a Guava 8-HT (Millipore; St Louis, Mo.) and Incyte software (Millipore) was utilized for data analysis. After gating on live lymphocytes, the percentage of NK cells was determined by the number of cells that were CD3 negative and CD16 and CD56 positive. For the HLA-DR$^{DIM}$ cells, gates were set on live cells, and CD14-positive cells and HLA-DR$^{DIM}$ cells were enumerated from the CD14-positive gate. The absolute numbers of autograft NK cells and autograft CD14$^+$HLA-DR$^{DIM}$ cells were calculated by multiplying their percentage times the A-ALC for NK cells and autograft absolute monocyte count (A-AMC) for CD14$^+$HLA-DR$^{DIM}$ cells for each apheresis unit collection. The A-ALC was calculated as follows: A-ALC=% collection lymphocytes×(absolute WBC/kg). In a similar manner, the A-AMC was calculated as follows: A-AMC=% collection monocytes×(absolute WBC/kg).

OS and PFS were analyzed using the approach of Kaplan-Meier (Kaplan and Meier 1958, J Am Stat Assoc 53:457-481). Differences between survival curves were tested for statistical significance using the two-tailed log-rank test. Univariate and multivariate analysis was performed using Cox proportional hazard model (Cox 1972, J R Stat Soc 34:187-202). The variables in the prognostic factor section were evaluated to assess their impact on OS and PFS times post APBHSCT. The choice of the cutoff value for the A-NKC/A-CD14$^+$HLADR$^{DIM}$ ratio to assess survival was based on its utility as a marker for the clinically relevant binary outcome of death/survival using the receiver operating characteristics curves (ROC) and area under the curve (AUC). The binary clinical outcome (death/survival) was established at 5 years after APHSCT. Patients were classified as 'alive/censored' when follow-up time was >5 years and 'death/uncensored' for patients known to have died before this time point (Tzankov et al. 2010, Leuk Lymphoma 51:199-212). A K-fold cross-validation with K-values of 10 was performed to validate the results of A-NKC/A-CD14$^+$HLA-DR$^{DIM}$ ratio cutoff obtained by the ROC and AUC curves. Randomly chosen subsets containing 90% of the cohort were used for training, and the remaining 10% were left for testing. The cross-validation process was then repeated 10 times. Based on this analysis, cross-validation AUC by the ROC was produced, representing the discriminating accuracy of A-NKC/A-CD14$^+$HLA-DR$^{DIM}$ ratio for the binary clinical outcomes of death/survival.

The $\chi2$ tests and Fisher's exact tests were used to determine relationships between categorical variables as appropriate. The Wilcoxon rank test was used to determine associations between continuous variables and categories and nonparametric tests were used to evaluate associations for continuous variables. All P-values represented were two sided and statistical significance was declared at P<0.05.

The median age at the time of APBHSCT was 57 years (range: 20-74). The distribution of additional baseline characteristics for this cohort is presented in TABLE 1. The median follow-up from APHSCT was 57.2 months (range: 2.1-84.6 months) and 62.6 months (range: 37.6-84.6 months) for patients who were alive (n=72). The day-100 transplantation-related mortality was 1.8% (2/111): one patient died because of septic shock and one patient died of acute respiratory distress syndrome. Other than the two patients who died in the first 100 days after APBHSCT, 35 patients died because of relapse/progression of lymphoma and two patients died of myocardial infarction.

Figure 2B:
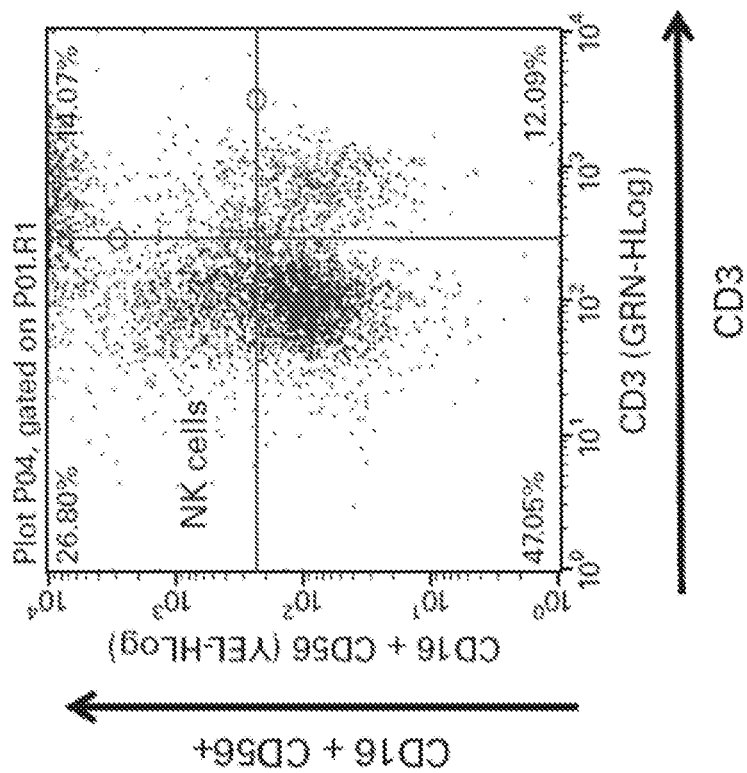
FIGS. 2A-2E are a series of fluorescence-activated cell sorting (FACS) scatter plots.
Figure 2A:
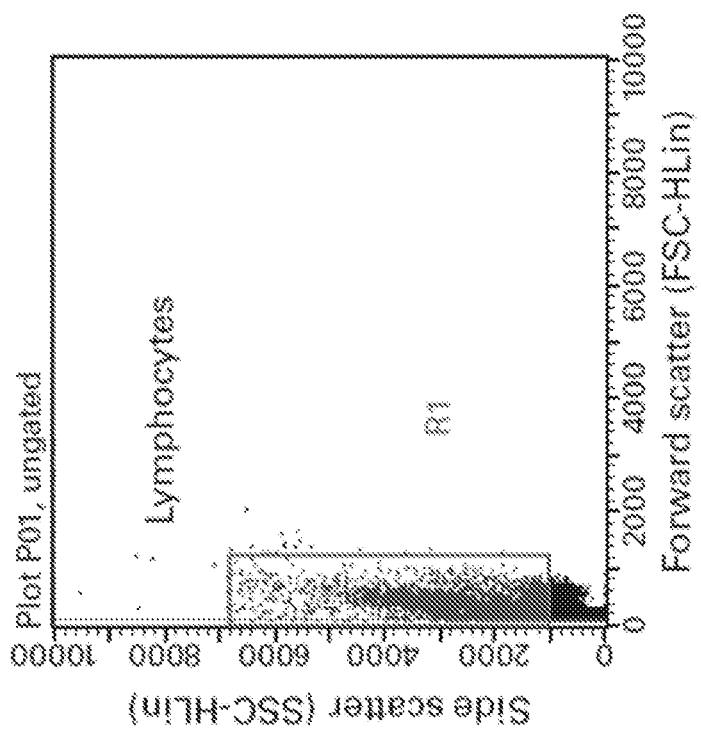
Figure 2D:
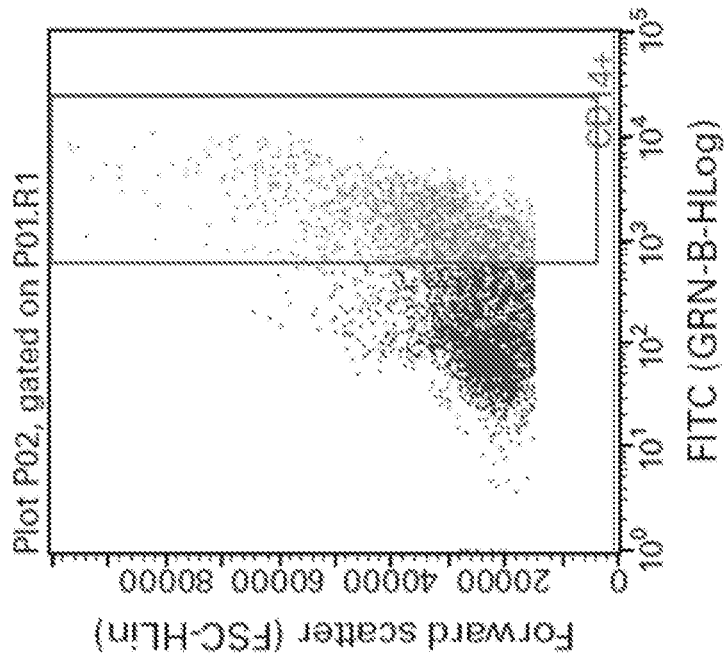
Figure 2C:
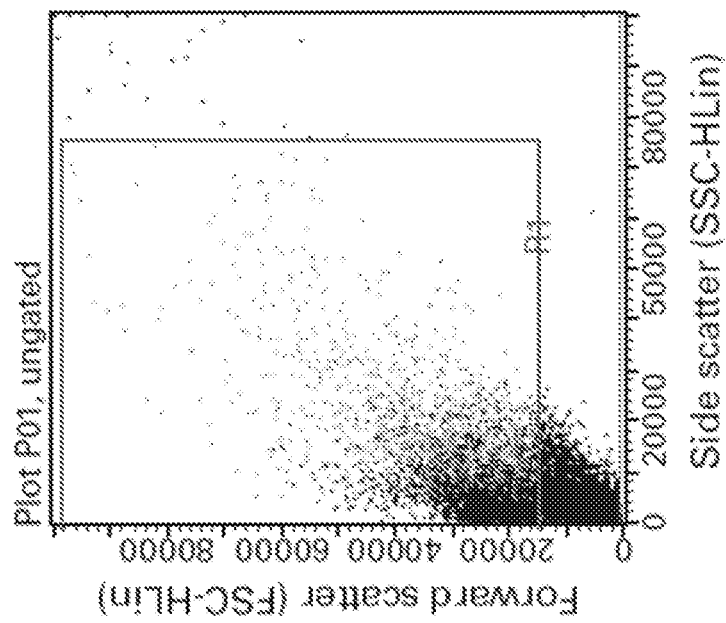
Figure 2E:
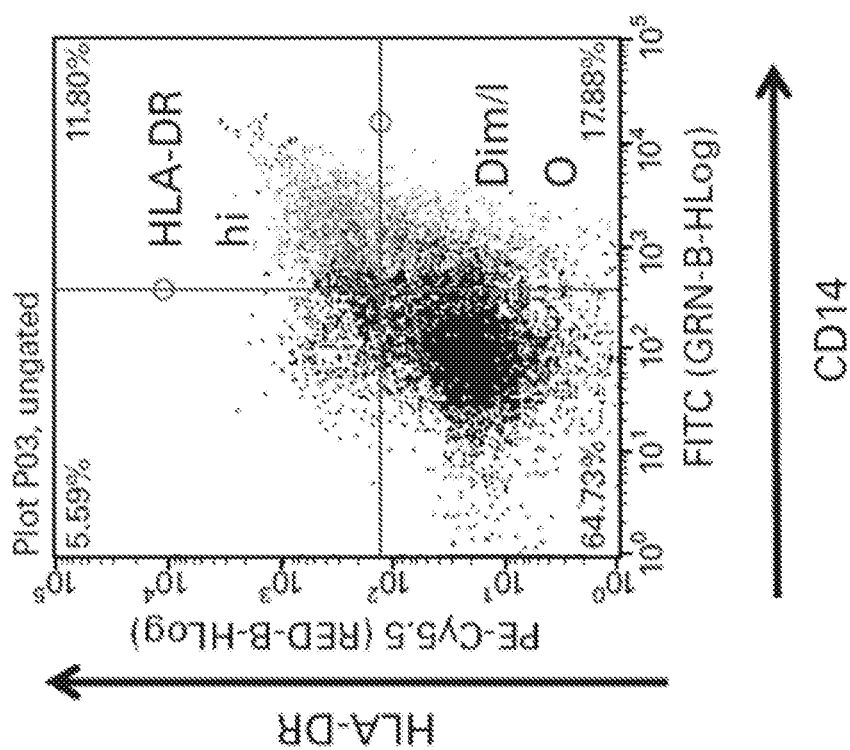
Figure 3A:
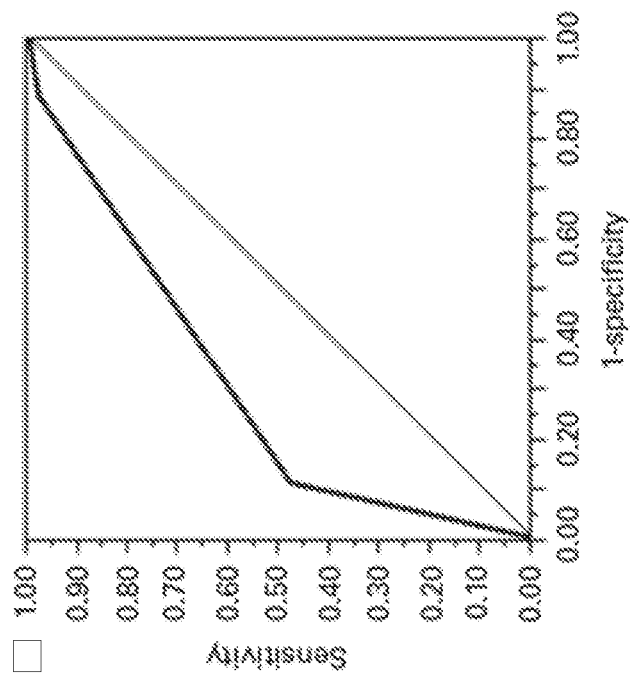
FIGS. 3A and 3B are graphs plotting the Receiver Operating Characteristic (ROC) and area under the curve (AUC) for A-NK:A-CD14+HLA-DR$^{DIM}$ ratio.

Representative fluorescence-activated cell sorting (FACS) plots to calculate the percentage of A-NKC are shown in FIGS. 2A and 2B, and representative FACS plots to calculate the percentage of A-CD14$^+$HLA-DR$^{DIM}$ FIGS. 2C-2E. ROC curves and AUC were used to determine the optimal cutoff points for A-NKC, A-CD14$^+$HLA-DR$^{DIM}$ and A-NK:A-CD14$^+$HLA-DR$^{DIM}$ ratio based on their utility as markers for the clinical binary outcome of death/survival. The A-NKC≥0.09×10$^9$ cells/kg had an AUC of 0.65 (95% CI, 0.59-0.71), with a sensitivity of 50% (95% CI, 45-55%) and a specificity of 81% (95% CI, 77-85%), P<0.04. The A-CD14$^+$HLA-DR$^{DIM}$≥0.21×10$^9$ cells/kg had an AUC of 0.74 (95% CI, 0.68-0.80), with a sensitivity of 49% (95% CI, 43-55%) and a specificity of 92% (95% CI, 85-99%), P<0.001. The A-NK:A-CD14$^+$HLA-DR$^{DIM}$ ratio≥0.29 had an AUC of 0.75 (95% CI, 0.70-0.80), with a sensitivity of 60% (95% CI, 55-65%) and a specificity of 89% (95% CI, 84-94%), P<0.0003 (FIG. 3A).

Figure 3B:
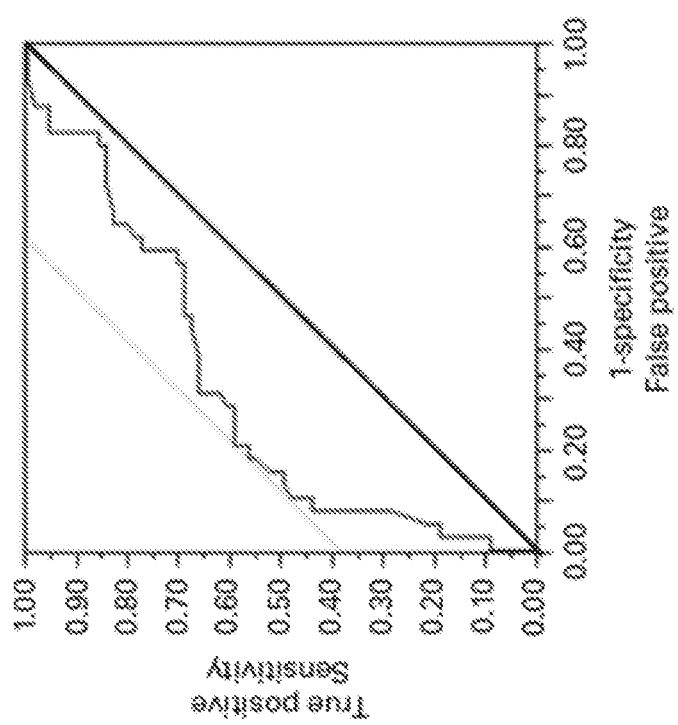

An internal validation of A-NKC, A-CD14$^+$HLA-DR$^{DIM}$ and A-NK:A-CD14$^+$HLA-DR$^{DIM}$ ratio performances as markers for the clinical binary outcomes of death/survival was performed using k-fold cross-validation with k=10. For A-NKC, the cross-validation ROC showed an AUC of 0.66 (95% CI, 0.66-0.72); for A-CD14$^+$HLA-DR$^{DIM}$, an AUC of 0.76 (95% CI, 0.71-0.81); and for A-NK:A-CD14$^+$HLA-DR$^{DIM}$ ratio, an AUC of 0.76 (96% CI, 0.70-0.82) (FIG. 3B). The similar AUC from the empirical ROC and the cross-validation ROC curves support the use of A-NKC≥0.09×10$^9$ cells/kg, A-CD14$^+$HLA-DR$^{DIM}$≥0.21×10$^9$ cells/kg, and the A-NK:A-CD14$^+$HLA-DR$^{DIM}$ ratio of ≥0.29 for cutoff values as markers of the binary clinical outcome of death/survival.

Based on the univariate Cox regression analysis, A-NK:A-CD14$^+$HLA-DR$^{DIM}$ ratio≥0.29 was a predictor for OS and PFS (see, TABLES 2A and 2B). A strong positive correlation was identified between A-NKC and A-NK:A-CD14$^+$HLA-DR$^{DIM}$ ratio≥0.29 (r=0.63, P<0.0001), and a strong negative correlation between A-CD14$^+$HLA-DR$^{DIM}$ and A-NK:A-CD14$^+$HLA-DR$^{DIM}$ ratio<0.29 (r=−0.70, P<0.0001). To avoid the problem of collinearity due to the strong correlation between A-NKC and A-NK:A-CD14$^+$HLA-DR$^{DIM}$ ratio, and between A-CD14$^+$HLA-DR$^{DIM}$ and A-NK:A-CD14$^+$HLA-DR$^{DIM}$ ratio, two separated multivariate analyses were performed. The first multivariate analysis included A-NKC and A-CD14$^+$HLA-DR$^{DIM}$ with the other prognostic factors in TABLES 2A and 2B, excluding the A-NK:A-CD14$^+$HLA-DR$^{DIM}$ ratio. In this first multivariate analysis, both were independent predictors for OS (A-NK: hazard ratio (HR)=0.34, 95% CI, 0.15-0.76, P<0.006; and A-CD14$^+$HLA-DR$^{DIM}$: HR=2.53, 95% CI, 1.12-6.05, P<0.03) and for PFS (A-NK: HR=0.31, 95% CI, 0.16-0.58, P<0.0001; and A-CD14$^+$HLA-DR$^{DIM}$: HR=2.05, 95% CI, 1.14-3.76, P<0.03). In the second multivariate analysis, A-NKC and A-CD14$^+$HLA-DR$^{DIM}$ were excluded, and the A-NK:A-CD14$^+$HLA-DR$^{DIM}$ ratio was included in the analysis. TABLE 3 shows that the A-NK:A-CD14$^+$HLA-DR$^{DIM}$ ratio was an independent prognostic factor for OS (HR=0.34, 95% CI, 0.16-0.68, P<0.002) and for PFS (HR=0.56, 95% CI, 0.32-0.96, P<0.03).

Patients were categorized into two groups (A-NK:A-CD14$^+$HLA-DR$^{DIM}$ ratio≥0.29 vs. A-NK:A-CD14$^+$HLA-DR$^{DIM}$ ratio<0.29) to assess whether both groups were balanced with regard to the baseline patient characteristics. As shown in TABLE 4, both groups were balanced, except for LDH, the disease status before APBHSCT, and the use of Plerixafor.

To evaluate survival outcomes based on A-CD14$^+$HLA-DR$^{DIM}$ and A-NK:A-CD14$^+$HLA-DR$^{DIM}$ ratio, A-CD14$^+$HLA-DR$^{DIM}$≥0.21×10$^9$ cells/kg and A-NK:A-CD14$^+$HLA-DR$^{DIM}$ ratio≥0.29 were tested for OS and PFS. Patients infused with an A-CD14$^+$HLA-DR$^{DIM}$<0.21×10$^9$ cells/kg vs. patients infused with an A-CD14$^+$HLA-DR$^{DIM}$≥0.21×10$^9$ cells/kg experienced superior OS (FIG. 4A) and PFS (FIG. 4B): median OS of not reached vs. 73.1 months, 5-year OS rates of 83% (95% CI, 70-95%) vs. 52% (95% CI, 39-56%), P<0.0005, respectively, and median PFS of not reached versus 31.1 months, 5-year PFS rates of 60% (95% CI, 47-72%) vs. 34% (95% CI, 22-47%), P<0.004, respectively. Further, patients infused with an A-NK:A-CD14$^+$HLA-DR$^{DIM}$ ratio≥0.29 vs. patients infused with an A-NK:A-CD14$^+$HLA-DR$^{DIM}$ ratio<0.29 experienced superior OS (FIG. 4C) and PFS (FIG. 4D): median OS of not reached vs. 56.2 months, 5-year OS rates of 84% (95% CI, 72-91%) vs. 48% (95% CI, 34-62%), P<0.0002, respectively; and median PFS of not reached vs. 31.1 months, 5-year PFS rates of 59% (95% CI, 46-71%) vs. 34% (95% CI, 22-47%), P<0.002, respectively.

Figure 4A:
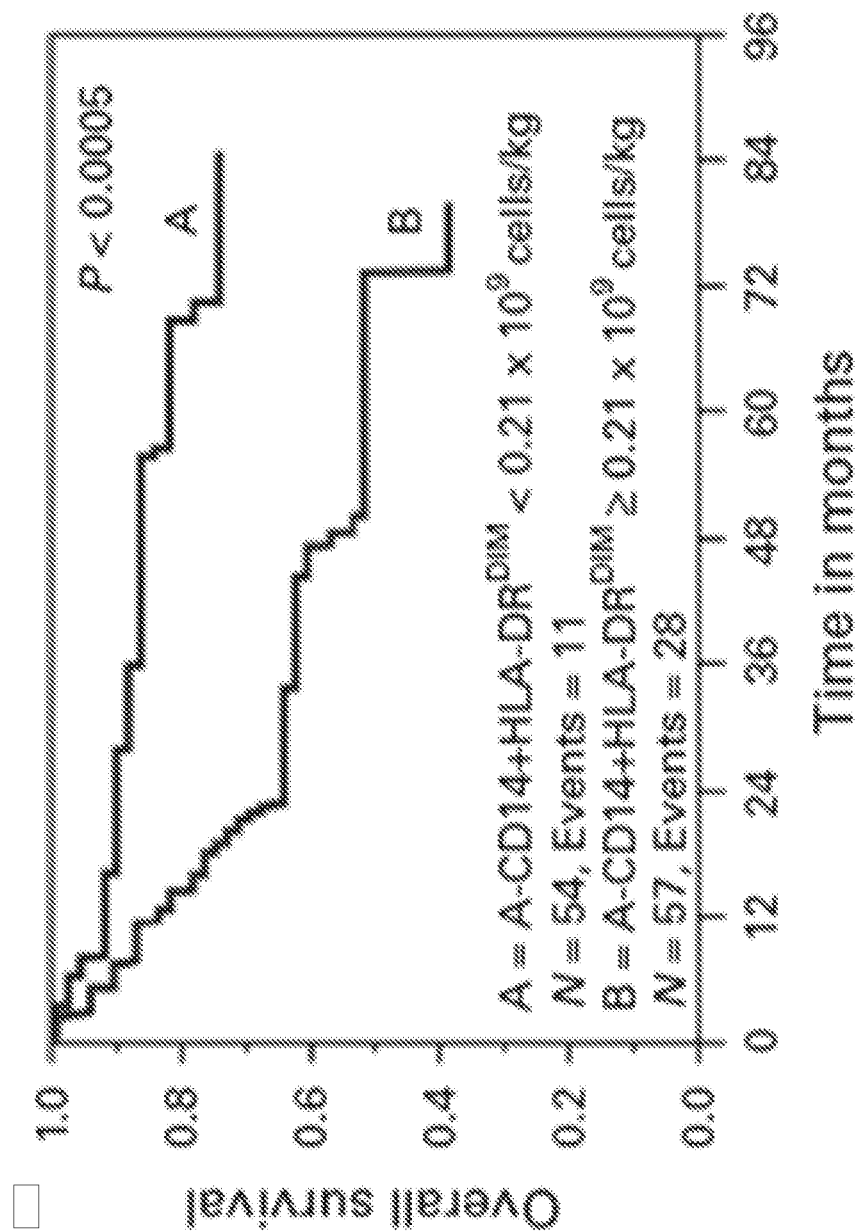
Figure 4B:
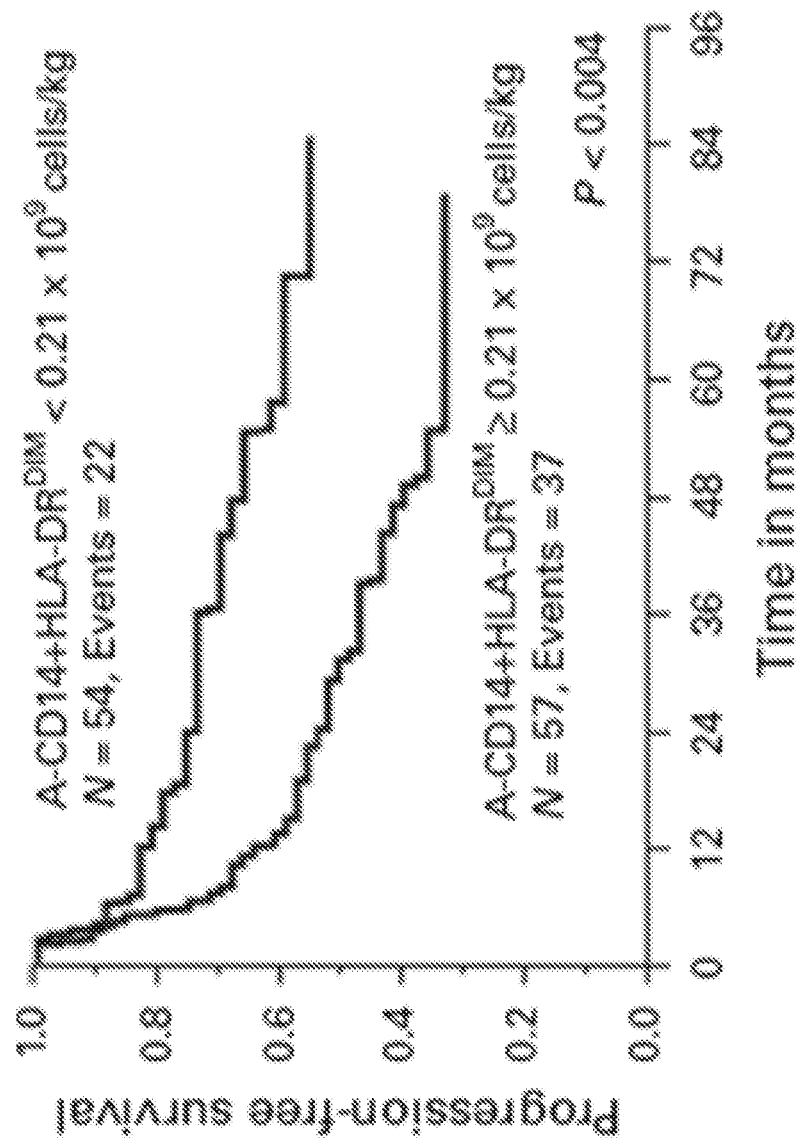
Figure 4D:
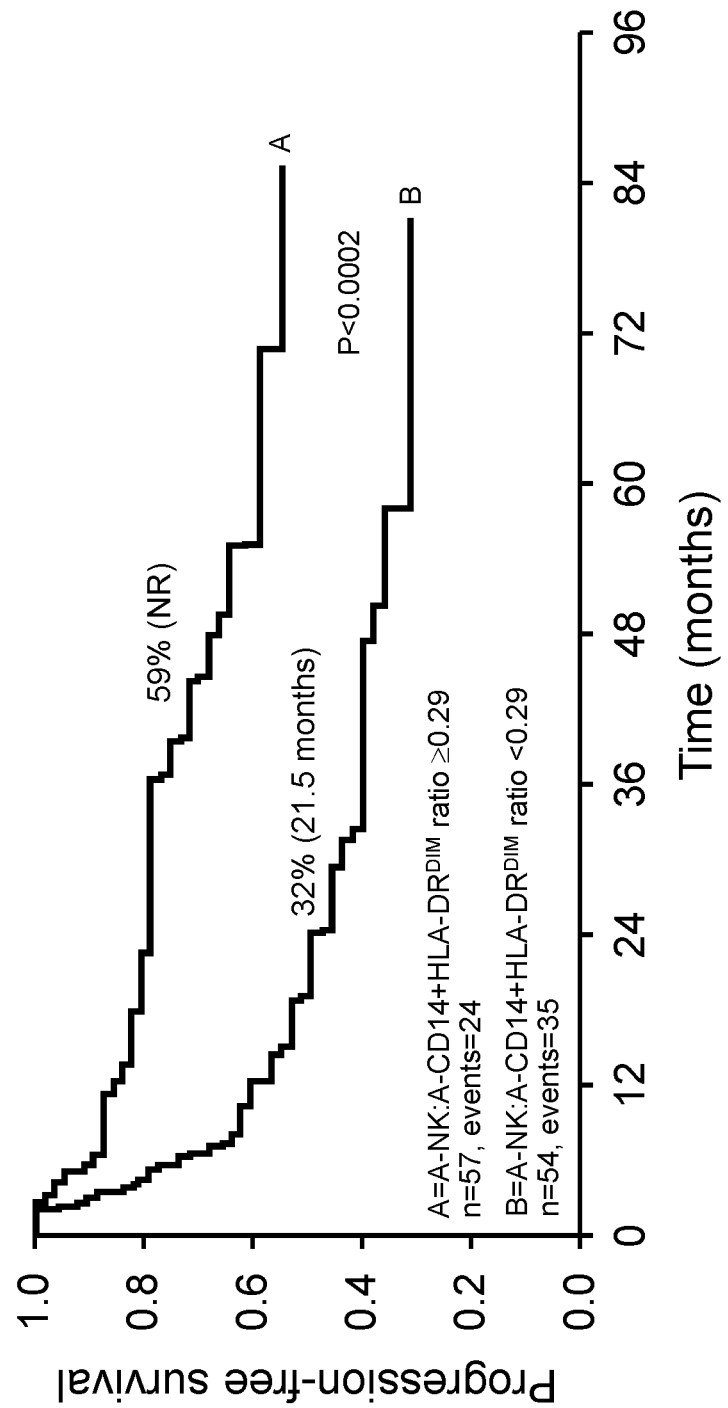

Patients with an IPI index of 0-2 experienced better OS and PFS with an A-NK:A-CD14$^+$HLA-DR$^{DIM}$ ratio≥0.29 compared with an A-NK:A-CD14$^+$HLA-DR$^{DIM}$ ratio<0.29, but patients with an IPI index of 3-4 did not (FIGS. 4A and 4B). For the subset of patients with DLBCL, those who received an A-NK:A-CD14$^+$HLA-DR$^{DIM}$ ratio≥0.29 experienced better OS and PFS than with patients with an A-NK:A-CD14$^+$HLA-DR$^{DIM}$ ratio<0.29 (FIGS. 4C and 4D). In the DLBCL group, the A-NK:A-CD14$^+$HLA-DR$^{DIM}$ ratio≥0.29 was an independent predictor for OS (HR=0.26, 95% CI, 0.16-0.43, P<0.0002) and PFS (HR=0.28, 95% CI, 0.18-0.55, P<0.0003).

TABLE 1

| Baseline patient characteristics | |
|---|---|
| Variables | N (%) |
| Age, year, median (range) | 55 (20-73) |
| Age, years | |
| ≤60 | 71 (64%) |
| >60 | 40 (36%) |

TABLE 1-continued

Baseline patient characteristics

| Variables | N (%) |
|---|---|
| Gender | |
| Male | 80 (72%) |
| Female | 31 (28%) |
| Histology | |
| DLBCL | 51 (46%) |
| Follicular lymphoma | 16 (14%) |
| Mantle cell lymphoma | 25 (23%) |
| Other | 19 (17%) |
| LDH (U/L), median (range) | 211 (106-3364) |
| LDH | |
| Normal | 58 (52%) |
| Abnormal | 53 (48%) |
| Stage | |
| I | 7 (6%) |
| II | 11 (10%) |
| III | 27 (24%) |
| IV | 66 (60%) |
| Stage | |
| I/II | 18 (16%) |
| III/IV | 93 (84%) |
| Extra-nodal disease | |
| 0 | 51 (46%) |
| 1 | 52 (47%) |
| 2 | 8 (7%) |
| Extra-nodal disease | |
| ≤1 | 103 (93%) |
| >1 | 8 (7%) |
| Performance status | |
| 0 | 28 (25%) |
| 1 | 71 (64%) |
| 2 | 12 (11%) |
| Performance status | |
| ≤1 | 99 (89%) |
| >1 | 12 (11%) |
| IPI score | |
| 0 | 15 (13%) |
| 1 | 34 (31%) |
| 2 | 32 (29%) |
| 3 | 25 (23%) |
| 4 | 5 (4%) |
| IPI Index | |
| ≤2 | 81 (73%) |
| >2 | 30 (27%) |
| At PBSC collection | |
| Age, years: median (range) | 57 (20-74) |
| Clinical status pre-transplant | |
| Complete response | 63 (57%) |
| Partial response | 48 (43%) |
| Number of chemotherapy regimens | |
| 1 | 35 (32%) |
| 2 | 65 (58%) |
| 3 | 7 (6%) |
| 4 | 3 (3%) |
| 5 | 1 (1%) |
| Apheresis machine | |
| ModC | 56 (50%) |
| StdC | 55 (50%) |
| Number of apheresis collections | |
| 1 | 8 (7%) |
| 2 | 22 (19%) |
| 3 | 24 (22%) |
| 4 | 25 (23%) |
| 5 | 17 (15%) |
| 6 | 5 (5%) |
| 7 | 8 (7%) |
| 8 | 2 (2%) |
| Plerixafor | |
| Yes | 44 (40%) |
| No | 67 (60%) |
| Infused CD34$^+$ cells × 10$^6$/kg: median (range) | 5.15 (2.02-11.37) |

TABLE 2A

| Dichotomized Variables | Overall survival | | | Progression-free survival | | |
|---|---|---|---|---|---|---|
| | HR | 95% CI | P | HR | 95% CI | P |
| Age >60 years | 1.55 | 0.81-2.93 | 0.2 | 1.18 | 0.69-1.97 | 0.5 |
| Elevated LDH | 2.40 | 1.26-4.74 | <0.007 | 1.56 | 0.94-2.62 | 0.09 |
| Stage III/IV | 1.50 | 0.69-4.38 | 0.4 | 2.72 | 1.20-7.82 | <0.01 |
| Extra-nodal involvement >1 | 5.312 | 2.12-11.60 | <0.001 | 3.35 | 1.38-6.97 | <0.01 |
| Performance status | 1.48 | 0.51-3.50 | 0.4 | 1.29 | 0.53-2.65 | 0.5 |
| IPI ≥2 | 2.27 | 1.18-4.28 | <0.02 | 1.81 | 1.04-3.05 | <0.04 |
| Complete vs partial response prior to transplant | 0.51 | 0.26-0.96 | <0.03 | 0.41 | 0.24-0.68 | <0.0001 |
| DLBCL vs other | 0.54 | 0.28-0.99 | <0.05 | 0.95 | 0.57-1.59 | 0.9 |
| Female vs male | 2.03 | 1.04-0.55 | <0.05 | 1.47 | 0.83-0.74 | 0.3 |
| A-NKC ≥0.09 × 10$^9$ cells/kg | 0.34 | 0.14-0.70 | <0.003 | 0.09 | 0.14-0.52 | <0.0001 |
| A-CD14 + HLA-DR$^{DIM}$ ≥0.21 × 10$^9$ cells/kg | 3.26 | 1.66-6.89 | <0.0005 | 2.14 | 1.27-3.69 | <0.004 |
| A-NK:A-CD14$^+$HLA-DR$^{DIM}$ ratio ≥0.29 | 0.28 | 0.14-0.55 | <0.0002 | 0.44 | 0.26-0.74 | <0.002 |
| Infused CD34 | 0.39 | 0.05-2.51 | 0.3 | 0.42 | 0.08-1.86 | 0.3 |
| Plerixafor | 1.32 | 0.69-2.53 | 0.4 | 1.35 | 0.80-2.27 | 0.3 |

TABLE 2B

|  | Overall survival | | | Progression-free survival | | |
| --- | --- | --- | --- | --- | --- | --- |
| Continuous Variables | HR | 95% CI | P | HR | 95% CI | P |
| A-NKC | 0.26 | 0.06-0.96 | <0.04 | 0.18 | 0.05-0.56 | <0.002 |
| A-CD14$^+$HLA-DR$^{DIM}$ | 5.83 | 1.86-15.97 | <0.004 | 2.92 | 1.07-7.07 | <0.04 |
| A-NKC/A-CD14$^+$HLA-DR$^{DIM}$ ratio | 0.07 | 0.01-0.30 | <0.0001 | 0.15 | 0.05-0.37 | <0.0001 |
| Infused CD34$^+$ cells | 0.39 | 0.05-2.51 | 0.3 | 0.42 | 0.08-1.86 | 0.3 |

TABLE 3

|  | Overall survival | | | Progression-free survival | | |
| --- | --- | --- | --- | --- | --- | --- |
| Variables | HR | 95% CI | P | HR | 95% CI | P |
| Female vs male | 1.84 | 0.92-3.56 | 0.08 | | | |
| Complete vs partial response prior to transplant | 0.55 | 0.27-1.05 | 0.09 | 0.65 | 0.37-1.14 | 0.1 |
| DLBCL vs other | 0.53 | 0.27-1.01 | 0.06 | | | |
| IPI ≥2 | 1.01 | 0.39-2.60 | 0.9 | 1.35 | 0.70-2.48 | 0.4 |
| A-NK:A-CD14 + HLA-DR$^{DIM}$ ratio ≥0.29 | 0.34 | 0.16-0.68 | <0.002 | 0.56 | 0.32-0.96 | <0.03 |
| Extra-nodal disease >1 | 3.23 | 1.06-9.47 | <0.04 | 2.07 | 0.77-5.13 | 0.1 |
| Elevated LDH | 1.54 | 0.63-3.59 | 0.3 | | | |
| Stage III/IV | | | | 1.87 | 0.78-5.55 | 0.2 |

TABLE 4

Baseline characteristics based on A-NK:A-CD14$^+$ HLA-DR$^{DIM}$ ratio

| Variables | A-NK:A-CD14 + HLA-DR$^{DIM}$ ≥0.29 (n = 57) | A-NK:A-CD14 + HLA-DR$^{DIM}$ <0.29 (n = 54) | P |
| --- | --- | --- | --- |
| Age, year, median (range) | 58 (20-74) | 56.5 (24-74) | 0.6 |
| Male | 41 (72%) | 39 (72%) | 0.9 |
| Female | 16 (28%) | 15 (28%) | |
| LDH (g/dL), median (range) | 190 (120-913) | 232 (106-365) | <0.04 |
| Extra-nodal disease | | | 0.2 |
| 0 | 29 (51%) | 22 (41%) | |
| 1 | 26 (45%) | 26 (48%) | |
| 2 | 2 (4%) | 6 (11%) | |
| Performance status | | | 0.7 |
| 0 | 16 (28%) | 12 (22%) | |
| 1 | 26 (63%) | 35 (65%) | |
| 2 | 5 (9%) | 7 (13%) | |
| Histologies | | | 0.9 |
| DLBCL | 25 (44%) | 26 (48%) | |
| Follicular | 8 (14%) | 8 (15%) | |
| Mantle cell | 13 (23%) | 12 (22%) | |
| Other | 11 (19%) | 8 (15%) | |
| Stage | | | 0.3 |
| I | 5 (9%) | 2 (4%) | |
| II | 8 (14%) | 3 (6%) | |
| III | 12 (21%) | 15 (28%) | |
| IV | 32 (56%) | 34 (62%) | |
| IPI score | | | 0.06 |
| 0 | 13 (22%) | 2 (4%) | |
| 1 | 16 (28%) | 18 (33%) | |
| 2 | 14 (25%) | 18 (33%) | |
| 3 | 12 (21%) | 13 (24%) | |
| 4 | 2 (4%) | 3 (6%) | |
| IPI risk factors | | | |
| Age, years | | | 0.8 |
| >60 | 20 (35%) | 20 (37%) | |
| ≤60 | 37 (65%) | 34 (63%) | |
| Extra-nodal disease | | | 0.2 |
| ≥2 | 2 (4%) | 6 (11%) | |
| <2 | 55 (96%) | 48 (89%) | |
| LDH | | | 0.3 |
| Abnormal | 24 (42%) | 29 (54%) | |
| Normal | 33 (58%) | 25 (46%) | |
| Performance status | | | 0.6 |
| 1 | 5 (9%) | 7 (13%) | |
| ≤1 | 52 (91%) | 47 (87%) | |
| Stage | | | 0.07 |
| I/II | 13 (23%) | 5 (9%) | |
| III/IV | 44 (77%) | 49 (91%) | |
| IPI Index | | | 0.7 |
| 2 | 14 (25%) | 16 (30%) | |
| ≤2 | 43 (75%) | 38 (70%) | |
| Clinical status pre-transplant | | | <0.003 |
| Complete response | 40 (70%) | 23 (43%) | |
| Partial response | 17 (30%) | 31 (57%) | |
| Plerixafor | | | <0.004 |
| Yes | 15 (26%) | 29 (54%) | |
| No | 42 (74%) | 25 (46%) | |
| Infused CD34 cells/kg, median (range) | 5.15 (2.0-11.37) | 5.14 (2.27-8.15) | 0.4 |
| Apheresis machine | | | 0.3 |
| ModC | 26 (46%) | 30 (56%) | |
| StdC | 31 (54%) | 24 (44%) | |
| Number of apheresis collections | | | 0.5 |
| 1 | 5 (9%) | 3 (6%) | |
| 2 | 9 (16%) | 13 (24%) | |
| 3 | 14 (25%) | 10 (18%) | |
| 4 | 11 (19%) | 14 (26%) | |
| 5 | 11 (19%) | 6 (11%) | |
| 6 | 3 (5%) | 2 (4%) | |
| 7 | 4 (7%) | 4 (7%) | |
| 8 | 0 (0%) | 2 (4%) | |

ModC = modified apheresis machine
StdC = standard apheresis machine

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a cancer patient, said method comprising administering a pharmaceutical composition comprising an immunotherapeutic agent to a cancer patient identified as having a biological sample with a natural killer (NK):CD14+HLA-DR$^{DIM}$ ratio less than 0.29, wherein the cancer is non-Hodgkin's lymphoma, and wherein the immunotherapeutic agent is IL-15, IL-21, or a combination thereof.

2. The method of claim 1, wherein the patient was identified based on a NK:CD14+HLA-DR$^{DIM}$ ratio determined at initial diagnosis of the cancer or prior to treatment.

3. The method of claim 1, wherein the patient has received an autologous peripheral hematopoietic stem cell transplantation (APBHSCT), and wherein the patient was identified based on a NK:CD14+HLA-DR$^{DIM}$ ratio calculated using absolute NK cell count and absolute CD14+HLA-DRD$^{DIM}$ count in a blood sample obtained from the patient after the APBHSCT.

4. The method of claim 1, wherein the patient was treated with chemotherapy, and wherein the patient was identified based on a NK:CD14+HLA-DR$^{DIM}$ ratio calculated using absolute NK cell count and absolute CD14+HLA-DRD$^{DIM}$ count within a blood sample obtained from the patient after the chemotherapy.

5. The method of claim 1, wherein the patient was identified as having a NK:CD14+HLA-DR$^{DIM}$ ratio less than 0.25.

* * * * *